US009119722B1

(12) United States Patent
Kusuma

(10) Patent No.: US 9,119,722 B1
(45) Date of Patent: Sep. 1, 2015

(54) MEASUREMENT AND PLACEMENT TECHNIQUES IN HIP RESURFACING AND THE LIKE

(76) Inventor: Sharat Kusuma, Columbus, OH (US)

( * ) Notice: Subject to any disclaimer, the term of this patent is extended or adjusted under 35 U.S.C. 154(b) by 484 days.

(21) Appl. No.: 13/401,165

(22) Filed: Feb. 21, 2012

Related U.S. Application Data

(60) Provisional application No. 61/525,104, filed on Aug. 18, 2011, provisional application No. 61/596,421, filed on Feb. 8, 2012.

(51) Int. Cl.
| | | |
|---|---|---|
| *A61B 17/56* | (2006.01) | |
| *A61B 17/74* | (2006.01) | |
| *A61B 17/88* | (2006.01) | |
| *A61F 2/36* | (2006.01) | |
| *A61B 17/16* | (2006.01) | |
| *A61F 2/32* | (2006.01) | |
| *A61F 2/34* | (2006.01) |

(52) U.S. Cl.
CPC .............. *A61F 2/36* (2013.01); *A61B 17/1664* (2013.01); *A61B 17/1666* (2013.01); *A61B 17/1668* (2013.01); *A61B 17/56* (2013.01); *A61B 17/74* (2013.01); *A61B 17/748* (2013.01); *A61F 2/32* (2013.01); *A61F 2/34* (2013.01); *A61B 17/742* (2013.01)

(58) Field of Classification Search
CPC ........ A61B 17/56; A61B 17/66; A61B 17/68; A61B 17/74; A61B 17/742; A61B 17/744; A61B 17/746; A61B 17/748; A61B 17/1664; A61B 17/1666; A61B 17/1668; A61B 2017/564; A61F 2/32; A61F 2/34; A61F 2/36; A61F 2/3609; A61F 2002/3656

USPC .................. 606/81, 86 R, 87, 89, 91, 96, 97; 623/22.11, 22.12, 22.15, 22.21, 22.4, 623/23.11, 23.12
See application file for complete search history.

(56) References Cited

U.S. PATENT DOCUMENTS

| | | |
|---|---|---|
| 4,715,860 A | 12/1987 | Amstutz et al. |
| 6,096,084 A | 8/2000 | Townley |
| 6,136,034 A | 10/2000 | Townley |
| 6,595,999 B2 | 7/2003 | Marchione et al. |
| 6,626,949 B1 | 9/2003 | Townley |
| 6,701,174 B1 | 3/2004 | Krause et al. |
| 6,711,432 B1 | 3/2004 | Krause et al. |
| 7,169,185 B2 | 1/2007 | Sidebotham |
| 7,361,194 B2 | 4/2008 | Carroll |
| 7,572,295 B2 | 8/2009 | Steinberg |
| 7,641,656 B2 | 1/2010 | Collins et al. |
| 7,695,476 B2 | 4/2010 | Nevelos |

(Continued)

*Primary Examiner* — Michael T Schaper
*Assistant Examiner* — Tracy Kamikawa
(74) *Attorney, Agent, or Firm* — Roger A. Gilcrest

(57) ABSTRACT

The present invention includes a measurement/assessment technique based upon a collection of angular and distance measurements taken with respect to x-ray visible osteo-anatomical artifacts to arrive at accurate and easily reproducible component placement. In the context of hip arthroplasty surgery the method of the present invention involves determinations, from two different two-dimensional views, of the angles and distances from osteo-anatomical artifacts, to allow a surgeon to approach a hip resurfacing operation with the distance and angular measurements to be translated into actual markings and device settings to be able to accurately ream the femoral head structure, position and affix the femoral cap and acetabular cup components in accordance with the pre-determined distance and angular measurements.

8 Claims, 22 Drawing Sheets

(56) References Cited

U.S. PATENT DOCUMENTS

| | | |
|---|---|---|
| 7,819,875 B2 | 10/2010 | Chana |
| 7,819,879 B2 | 10/2010 | Penenberg |
| 7,837,621 B2 | 11/2010 | Krause et al. |
| 7,867,281 B2 | 1/2011 | Carroll |
| 7,879,106 B2 | 2/2011 | McMinn |
| 7,885,705 B2 | 2/2011 | Murphy |
| 7,887,831 B2 | 2/2011 | Yayon |
| 7,909,882 B2 | 3/2011 | Stinnette |
| D642,263 S | 7/2011 | Park |
| 8,078,440 B2 | 12/2011 | Otto et al. |
| 2006/0189864 A1 | 8/2006 | Paradis et al. |
| 2008/0004710 A1 | 1/2008 | Ledger et al. |
| 2008/0009951 A1 | 1/2008 | Hodge |
| 2008/0033577 A1 | 2/2008 | Kohan |
| 2008/0109085 A1 | 5/2008 | Tulkis et al. |
| 2008/0125785 A1 | 5/2008 | Chana |
| 2008/0200991 A1 | 8/2008 | Collins et al. |
| 2008/0262626 A1 | 10/2008 | Raugel |
| 2009/0048681 A1 | 2/2009 | Vlachos |
| 2009/0222015 A1 | 9/2009 | Park |
| 2010/0121458 A1 | 5/2010 | Ledger et al. |
| 2010/0125340 A1 | 5/2010 | Ure |
| 2010/0274253 A1 | 10/2010 | Ure |
| 2011/0004318 A1 | 1/2011 | Tulkis et al. |
| 2011/0190775 A1 | 8/2011 | Ure |

MEASUREMENT AND PLACEMENT TECHNIQUES IN HIP RESURFACING AND THE LIKE

RELATED APPLICATION DATA

This application claims the priority benefit of U.S. Provisional Application Ser. No. 61/525,104, filed Aug. 18, 2011, and U.S. Provisional Application Ser. No. 61/596,421, filed Feb. 8, 2012, which are hereby incorporated in their entirety herein by reference.

FIELD OF THE INVENTION

The present invention relates to measurement and placement techniques used in joint replacement surgery, such as resurfacing hip-joint implants and the like, as well as to surgical operations carried out using the described techniques.

BACKGROUND OF THE INVENTION

A natural hip joint may undergo degenerative changes due to a variety of etiologies. When these degenerative changes become so far advanced and irreversible, it may ultimately become necessary to replace a natural hip joint with a prosthetic hip.

Various partial or complete replacements of the hip joint have been proposed and used since the early 1900's. Most of the procedures or methods involved material problems that led to joint loosening and consequential failure.

One widely used total hip replacement removes the femoral head and inserts a stem into the upper end of the femur, where it is fixed either by cement or by bone growth into a porous coating. A small metal ball, replacing the patient's femoral ball, is affixed to the stem. This technique requires massive bone removal and results in extreme loading of force in a leveraging action from the top of the femoral ball to a lower part of the stem. Over a few years, force applied by vigorous and mostly younger patients can cause the stem to loosen, resulting in failure, pain and need for extensive and expensive revisions. Additionally, such hips that use large femoral stems with metal on plastic articulations have had problems with dislocation due to small head sizes, as well as wear of the polyethylene acetabular components that have resulted in relatively rapid failures.

This need has led to the development of metal on metal femoral resurfacing components that require only that a portion of the femur head be resected or resurfaced, rather than the entire femur head. An early example of such an operation was developed by Derek McMinn, M.D. and Ronan Treacy, M.D. in Birmingham, England in the early 1990s.

One of the significant challenges of more general adoption of hip resurfacing is the accurate positioning of the femoral cap and its alignment with respect to the resurfaced femoral head, as well as the complementary alignment and positioning of the concave, hemispherical acetabular insert piece with which the femoral cap cooperates.

One of the major issues with adoption of this procedure in the United States over the past 6 or 7 years has been extremely difficult achieving appropriate component positioning. See Nunley et al., CORR 2010, Berend et. al JBJS 2011. (hereby incorporated herein by reference).

Accurate and reproducible component positioning is very challenging because the constituent joint bones are very irregularly shaped, and do not lend themselves to easy measurement in all of the dimensions necessary to resurface and reintroduce the bones into a cooperative, jointed disposition. After the dimensions and orientation of the femur and pelvic joint portions are approximated, the dimensions must then be changed by the reaming process in preparation for the resurfacing operation. To complete the operation, the correctly sized synthetic components must be installed to best fit the originally approximated femoral and pelvic dimensions.

Further complicating this process is that the surgeon must be able to operate under time constraints while performing the approximation and resurfacing procedures while the constituent bones are removed from their normal position, and freed from their surrounding soft tissue.

Various methods have been tried for this including computer navigation with very expensive computer navigation technology from companies such as Brain Lab. Other methods involve the use of physical devices such as sizing template devices.

Notwithstanding attempts by others to improve upon the required measurement and placement processes involved in hip resurfacing operations, the literature currently reflects a learning curve of nearly 100 to 150 cases for surgeons to gain adequate component positioning experience to be proficient. Several papers relate that even experienced hip surgeons will require at least 50 to 75 cases to achieve adequate component positioning with this Birmingham hip surfacing operation. See Nunley et al., CORR 2010. Such long learning curves extend the period during which there is a risk of less than optimal placement and installation, often requiring additional surgery to ultimately obtain a satisfactory result.

Accordingly, there remains a need for an accurate, inexpensive and reproducible method for the placement of hip resurfacing components that allows a surgeon to relatively quickly become highly proficient in the placement, sizing and installation of these components in hip arthroplasty surgery.

SUMMARY OF THE INVENTION

The present invention includes a measurement/assessment technique based upon a collection of angular and distance measurements taken with respect to x-ray visible osteo-anatomical artifacts to arrive at accurate and easily reproducible component placement.

The present invention allows for the very accurate and appropriate component positioning for a hip resurfacing operation.

In the context of hip arthroplasty surgery the method of the present invention involves determinations, from two different two-dimensional views, of the angles and distances from osteo-anatomical artifacts, to allow a surgeon to approach a hip resurfacing operation with the distance and angular measurements to be translated into actual markings and device settings to be able to accurately ream the femoral head structure, position and affix the femoral cap and acetabular cup components in accordance with the pre-determined distance and angular measurements.

The present invention thus greatly accelerates the learning curve for this procedure while achieving outstanding component positioning much better than what has been documented in the literature previously.

In general terms, the method of the present invention includes a method of positioning components during the course of a hip resurfacing operation for a patient, involving the affixation of a femoral cap to the femoral head and the affixation of an acetabular component implant in the corresponding reamed and prepared acetabulum cup of the pelvis, the steps comprising, without respect to order as consistent with the obtained measurements: (a) in a scaled anterior-posterior x-ray image of the femur and pelvic region: (i)

providing a center line along the center axis of the femoral neck so as to indicate the position of the femoral lateral pin entry point and the location of the point of intersection of the center line with the superior femoral head surface; (ii) measuring the varus/valgus angle of the femoral neck with respect to the femur so as to determine the desired varus/valgus angle of insertion of the femoral component with respect to the femoral neck; (iii) providing additional lines parallel to the center line that are placed at the superior and inferior cortical margins of the femoral neck; these lines provide the surgeon with lower limits of bone resection for placement of the femoral cap without causing any damage to the femoral neck so as to determine the desired size of the femoral cap to be installed and thereby to permit the determination of the size of the femoral reamer to be used in the hip resurfacing operation; (iv) measuring the maximum diameter of the femoral neck that is determined by the placement of the parallel lines described in step (iii); (v) determining the notching distance corresponding to the superior femoral head and superior femoral neck positions (such notching distance being the exact distance from the exit point of the reamer device used to prepare the femoral head for the receipt of the resurfacing femoral cup to the cortical bone of the femoral neck, an area also referred to as the femoral neck "saddlepoint" and/or the piriformis fossa); (vi) determining the vertical distance from the tip of the greater trochanter to the lateral pin entry point; (vii) determining the exact location of the entry point of the lateral jig anchoring pin in relation to the cranial-caudal dimension of the lessor trochanter; (viii) determining the distance from the point of intersection in step (i) to the superior point of fovea on the femoral head; and (ix) measuring the cup closure angle so as to match the femoral head varus/valgus so as to facilitate combined abduction; the combined abduction being such that the face of the acetabular component is perfectly perpendicular to the center axis of the femoral component; and, (b) in a scaled lateral x-ray image of the femur and pelvic region: (i) drawing a centering line in the center of the femoral neck so as to select the anteversion/retroversion angle of the femoral head, and measuring the length of the centering line anterior to posterior; (ii) measuring both the anteversion angle of this centering line as well as the distance/position of the exit point of this line from the anterior and posterior margins of the femoral head; and (iii) calculating the anteversion of the centering line with respect to the shaft of the femur; the anteversion of the femoral component is then being used to calculate a target combined anteversion of between 30 and 45 degrees for the acetabular and femoral components; whereby the positioning parameters attendant to a hip resurfacing operation alignment are determined.

The method of the present invention includes the additional step of reaming the femoral head with a reamer the size of which is determined by reference to the parallel lines.

The method also includes performing the steps of and completing a hip resurfacing operation in accordance with the hip resurfacing operation positioning parameters. This will typically be done by marking the femur of the patient in accordance with the measurements taken in steps (a) and (b), and inserting a femoral cap in the patient using the angular measurements taken in steps (a) and (b).

The present invention also includes resurfaced hip joint components comprising a femoral cap and an acetabular cup, the femoral cap and acetabular cup positioned in a patient in accordance with the method of the present invention as described and claimed herein.

In addition, the invention includes the creation of a digital display reflecting those parameters, as well as the use of the displays to guide the intended surgery.

The foregoing and other objects, features, and advantages of this invention will become more readily apparent from the following detailed description of a preferred embodiment which proceeds with reference to the accompanying drawings, wherein the preferred embodiment of the invention is shown and described, simply by way of illustration of the best mode contemplated of carrying out the invention.

As will be realized, the invention is capable of other and different embodiments, and its several details are capable of modifications in various obvious respects, all without departing from the invention. Accordingly, the drawings and description are to be regarded as illustrative in nature, and not as restrictive. It will also be appreciated that the detailed description represents the preferred embodiment of the invention, and that individual steps of the process of the invention may be practiced independently so as to achieve similar results.

DETAILED DESCRIPTION OF THE PREFERRED EMBODIMENTS

In accordance with the foregoing summary, the following provides a detailed description of the preferred embodiment, which is presently considered to be the best mode thereof.

Figure 1:
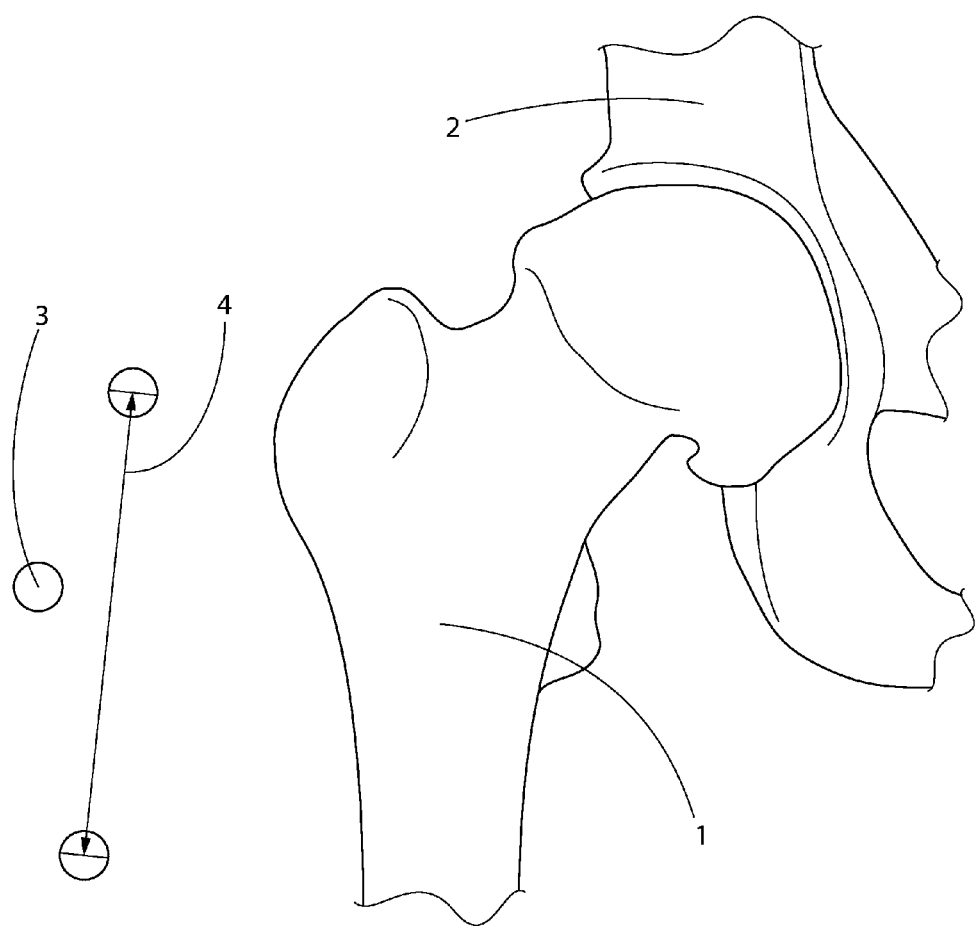
FIG. 1 is an x-ray image showing image scaling, a first step in the measurement and component placement process, in accordance with one embodiment of the present invention.

FIG. 1 is an x-ray image showing image scaling, a first step in the measurement and component placement process, in accordance with the described embodiment of the present invention. This shows the scaling process whereby the marker ball device is used to confirm the scaling/sizing of the x-ray. The first step of the technique is best performed on very detailed and high quality anterior or posterior pelvis radiographs as well as anterior and posterior radiographs of the affected hip along with a lateral x-ray of the affected hip. This may typically be obtained from an image stored in the electronic medical records of the patient, such as a Picture Archiving and Communication System (PACS) radiology system (such as, for example, the Synapse system commercially available from Fuji USA or the NovoPACS system commercially available from Novorad).

FIG. 1 shows the femur 1 and pelvis 2 as seem in an anterior-posterior view.

FIG. 1 also shows the preferred use of a marker article, such as a marker ball in order that the scaling of the image may be calibrated to allow accurate distance measurements. FIG. 1 shows the x-ray position of the radiographic marker ball 3 that has been calibrated, and placed on the x-ray beam. Also shown in FIG. 1 is a distance measurement line 4 with a numerical indication of line length.

Typically and preferably, the x-rays are accessible by a PACS radiology system. These systems have very simple software tools that allow marking and measurement of an x-ray image, such as angle measurement tools, ruler measurement tools, calibration tools, and an arrow device. After these x-rays have been completed and have been downloaded into the system, the steps that continue are as follows:

The first step is to use the anterior-posterior (AP) x-ray of the affected hip and confirm that the rotation of the leg is appropriate for imaging. For instance, many patients who have severe arthritis will have difficulty with the internal rotation required to allow appropriate AP x-ray of the affected hip. Therefore, typically one must confirm that the affected hip has been imaged correctly. Once this has been confirmed, the next step is for the operator (e.g., physician or other health care practitioner) to utilize the calibrated marker to measure the distance and assess the exact calibration of the x-ray. In most American systems, the x-ray calibration is roughly 20% over-magnified from standard whereas in most English and European systems this number is about 15%.

Figure 2:
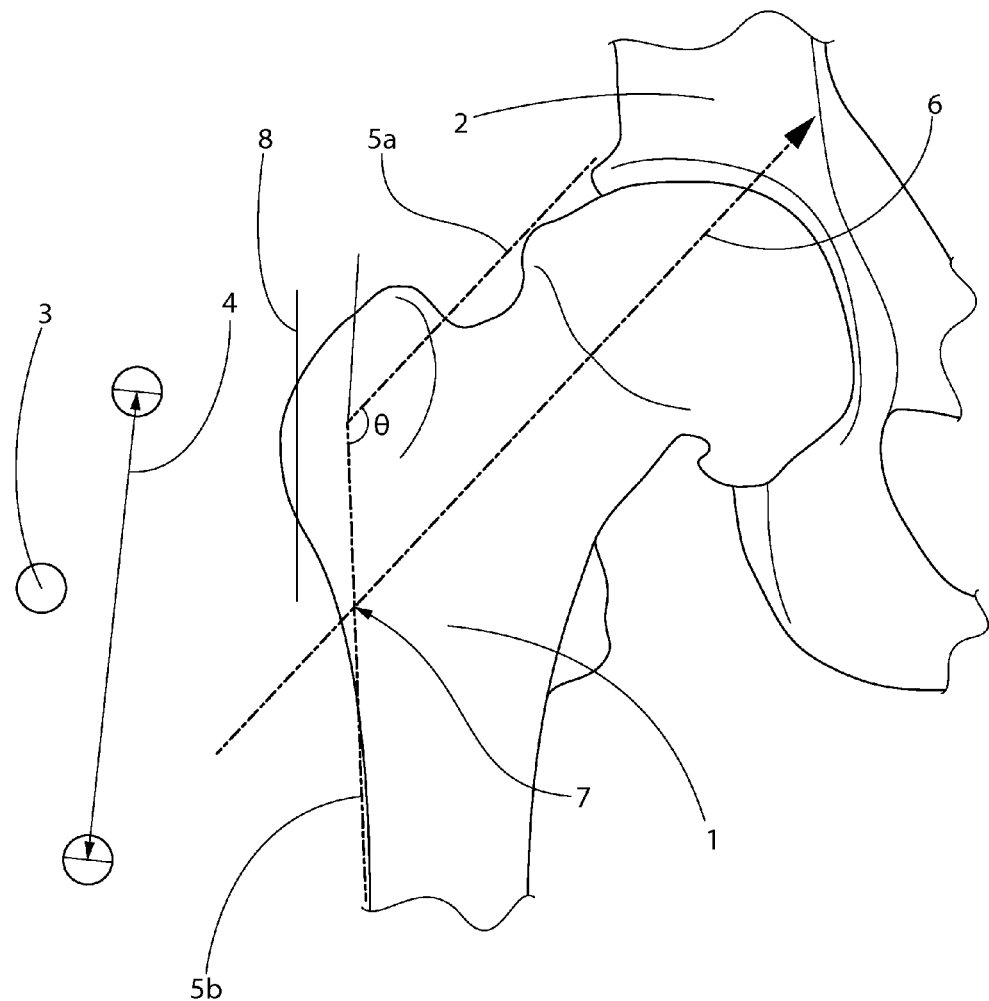
FIG. 2 is an x-ray image showing femoral neck varus/valgus angle determination, a second step in the measurement and component placement process, in accordance with one embodiment of the present invention.

FIG. 2 is an x-ray image showing the femoral neck varus/valgus angle determination, a second step in the measurement and component placement process, in accordance with the described embodiment of the present invention, and wherein the same numerals refer to the same objects, elements and features.

Once the imaging of the hip region has been confirmed, the next step involves the operator utilizing the arrow tool on the PACS device to draw an arrow 5a (or other linear indication) down the center of the femoral neck and the measurement of the angle this line forms in relation to the shaft of the femur where it intersects line 5b drawn alongside the femur, so as to match the varus/valgus angle (i.e., an angle 8 of approximately 136 degrees as shown in FIG. 2) of the femoral neck and, preferably, is slightly in an increased valgus. The operator has the ability with this step to choose the amount of varus or valgus that the surgeon would like to use for the femoral component positioning.

Once this is done, the surgeon or other operator again will draw a long arrow 6 (or other linear indication) that intersects the femoral neck down its mid-shaft and is in slight valgus orientation with regard to the patient's native femoral neck valgus. The operator may then identify the lateral exit point 7 of this arrow on the lateral femur and then utilize a ruler tool to measure the distance 8 from the tip of the greater trochanter down to the exit point 7 on the lateral femur. The surgeon or other operator will then draw a horizontal line across the femoral shaft that is perpendicular to the long axis of the femur [not shown] and again, he will use this line to measure the distance from the top of the greater trochanter down to the line drawn. This will provide the surgeon with a visual landmark of where and approximately how low on the lesser trochanter this line intersects. Intraoperatively, the surgeon can then use this laterally measured distance to measure in the operating room with a ruler (or other device) and place the lateral pin for the Birmingham hip resurfacing long arm jig onto the femur. So this is the first necessary step in this embodiment.

Figure 3:
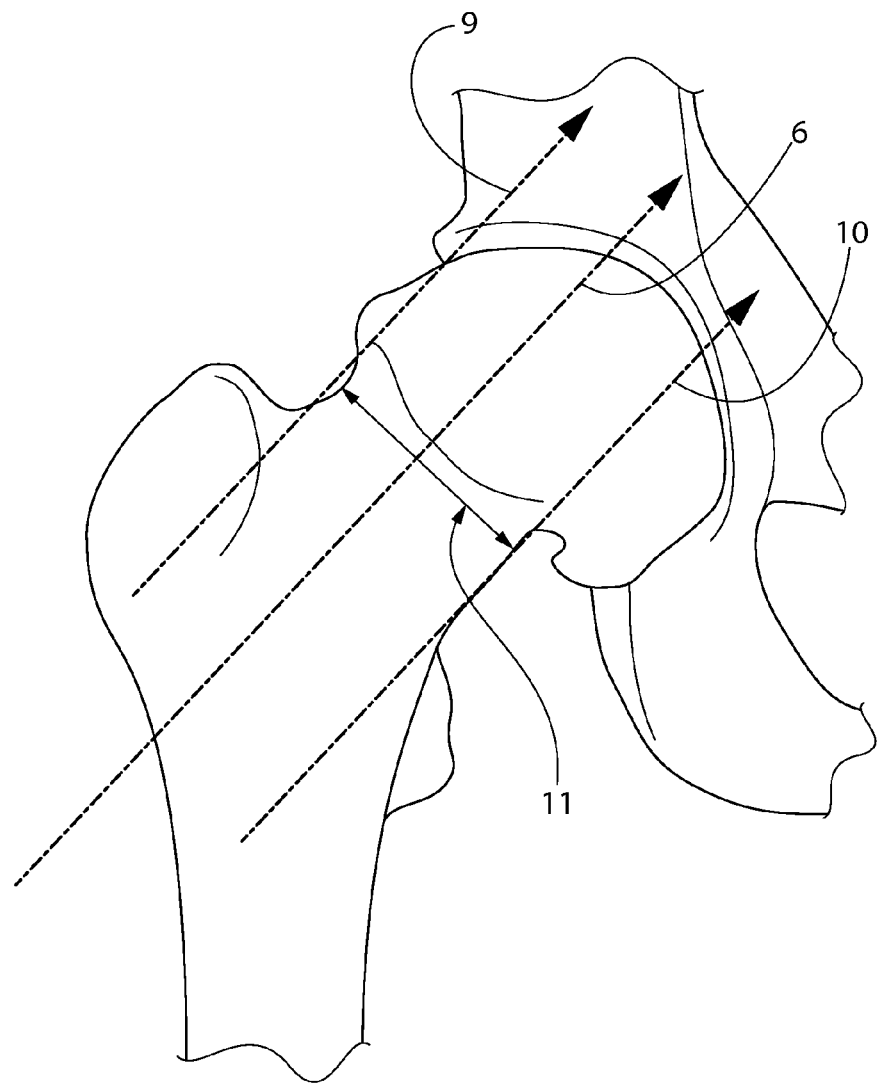
FIG. 3 is an x-ray image showing delineation of the femoral neck boundaries, another aspect of the second step in the measurement and component placement process, in accordance with one embodiment of the present invention.

The second necessary step in this embodiment is then to draw additional lines, such as lines 9 and 10, parallel to the center line 6. The surgeon or other operator should draw two lines parallel to the initial arrow 6 that will determine the maximum diameter of the femoral neck and how much femoral head bone will be reamed away by the barrel reamers that are eventually used. Preferably, there should be at least one line superior and one line inferior to the femoral neck as shown in FIG. 3. These lines will assist in confirming the position of the femoral cap component.

This may be referred to this as the "railroad track" technique as the lines 9 and 10 drawn appear to be like railroad tracks. These railroad track lines are placed at the superior and inferior cortical margins of the femoral neck; they provide the surgeon with lower limits of bone resection from the superior and inferior for placement of the femoral cap without causing any damage to the femoral neck. These lines will help the surgeon determine how closely the superior barrel reamer teeth will engage the cortical bone of the femoral head, and how much distance there will be from the exit point of the reamer superiorly until the barrel reamer contacts the superior femoral neck (which might lead to the formation of a notch). This railroad track technique is a very important landmark for the surgeon to allow him/her to determine more accurately how much room there is from the point that the barrel reamer exits the superior femoral neck until it notches and also the minimum inner diameter of the resurfacing barrel reamer that may be used without causing damage to the femoral neck.

Figure 4:
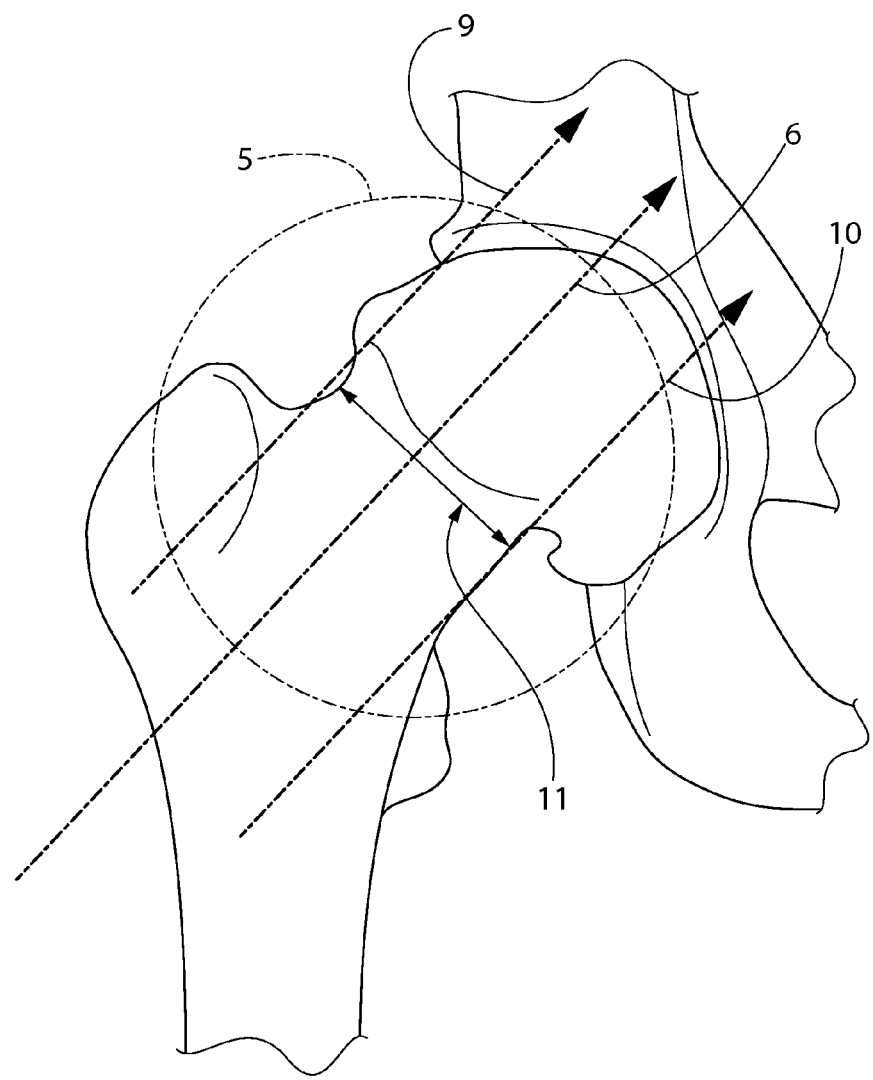
FIG. 4 is an x-ray image showing sizing of the femoral neck for reamer selection, another aspect of the second step in the measurement and component placement process in accordance with one embodiment of the present invention.
Figure 5:
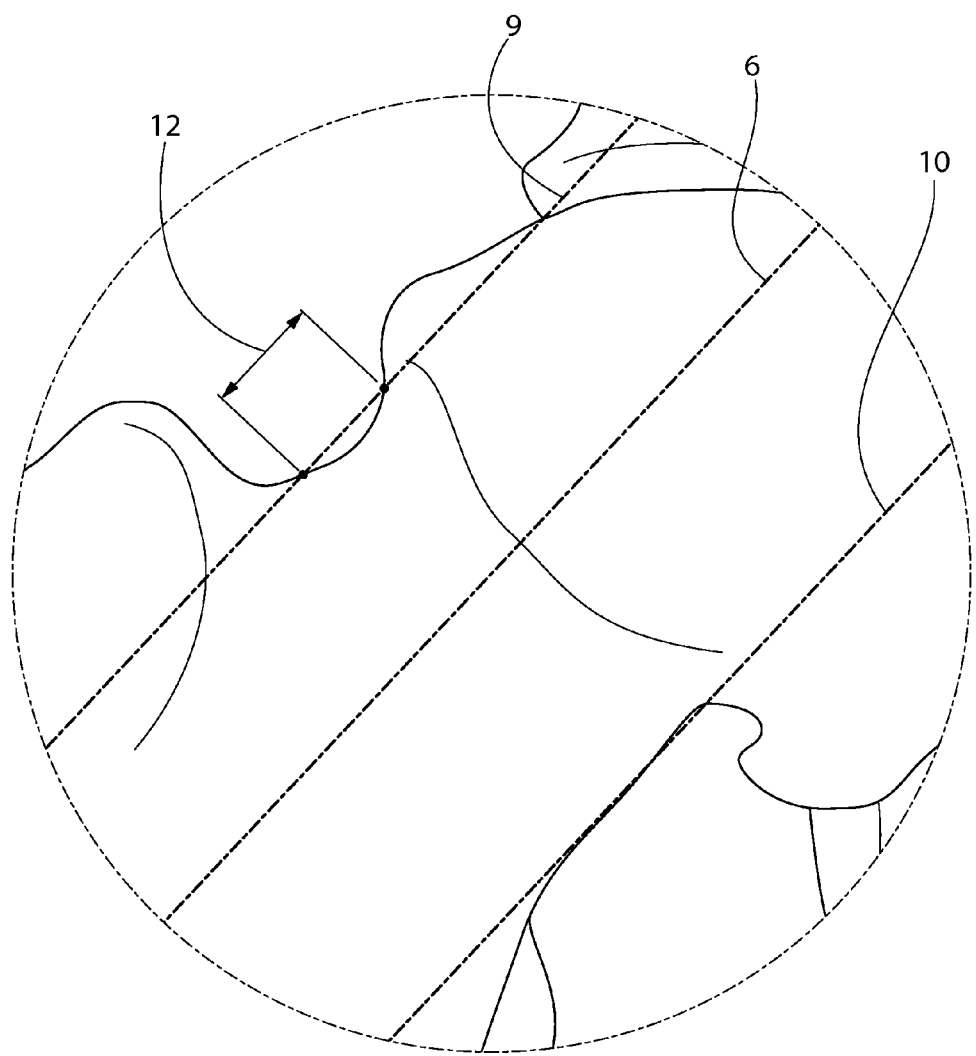
FIG. 5 is an x-ray image showing determination of the notching distance, another aspect of the second step in the measurement and component placement process, in accordance with one embodiment of the present invention.

This aspect of the method may be appreciated from FIG. 4 which is an x-ray image showing the second step in the measurement process wherein railroad track lines 9 and 10 establish a distance between them (see line 11; i.e., having a length of 38.71 mm) that represents an accurate measurement of the maximum head size admissible to the given patient's anatomy while minimizing the risk of notching of the femoral neck. Lines 9 and 10 indicate to the surgeon the minimum inner diameter of the reamer that the femoral neck can accommodate without being damaged by the reamer. In addition, FIG. 5 is a more detailed x-ray view of the determination of the so-called "notch distance" or the distance along line 9 where the barrel reamer would exit the superolateral femoral head and prior to encountering the superolateral femoral neck. In the example shown in FIG. 5, this distance 12 is 10.40 mm. This distance lets the operating surgeon know how much room is available to him/her for excursion of the reamer in a caudal direction before he/she will create a "notch" or point of damage on the superolateral femoral neck. Such notches are strongly associated with femoral neck fracture after a resurfacing procedure and are one of the most common technical mistakes committed by surgeons performing this procedure.

This railroad track technique will also help the surgeon determine the size of the head cap component that can be placed onto the patient's femoral head. Ideally, the railroad track lines 8 and 9 should spread as far apart as possible so that they are overlying the superior inferior femoral neck cortical bone; resulting in the measurement of the head size that can be applied to the given patient.

Figure 6:
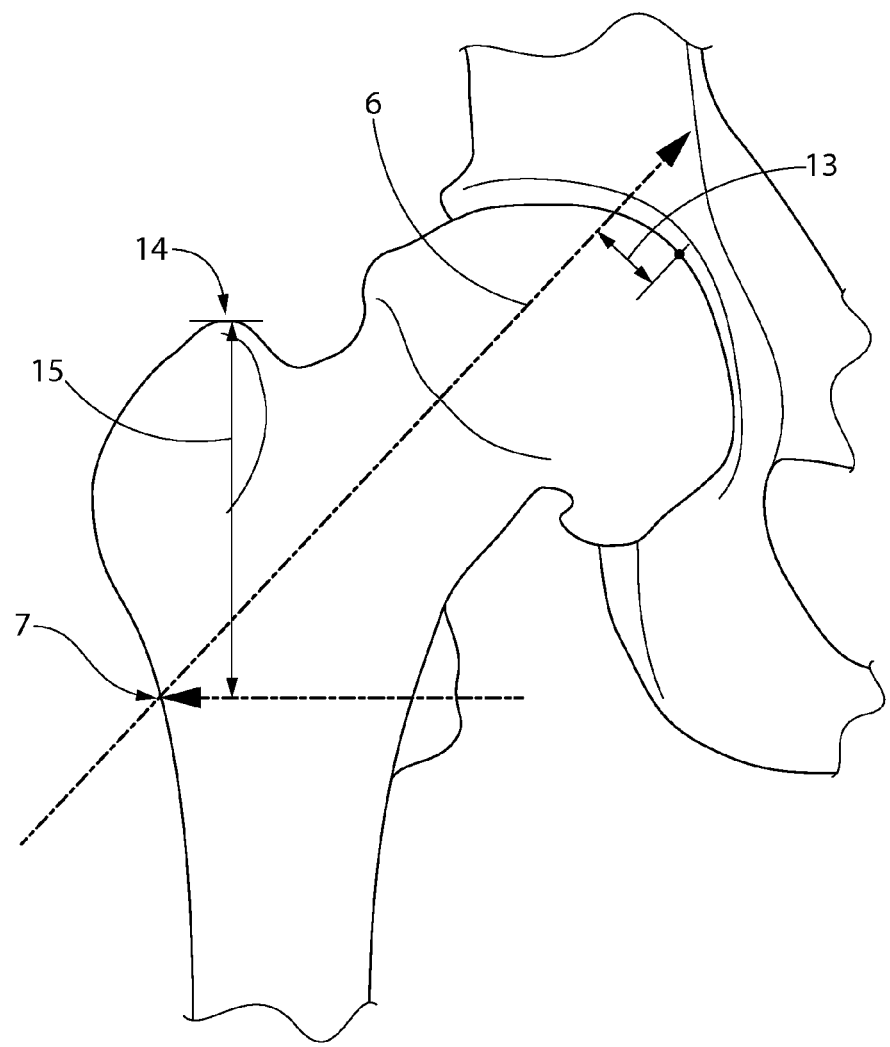
FIG. 6 is an x-ray image showing determination of an anchor point for the femoral jig, a third step in the measurement and component placement process, in accordance with one embodiment of the present invention.

Once this step is complete, the next step is for the operator to determine an anchor point for the femoral jig, as shown in FIG. 6. This may be approached in several ways.

FIG. 6 shows this third step being achieved through the measurement of the vertical distance 15 from the uppermost extent 14 of the greater trochanter to the height of the established exit point 7 of the lateral pin. In the example shown in FIG. 6, this distance 15 is 62.34 mm. In summary, this illustrates the measurement of the distance from the tip of the greater trochanter to the placement point of a pin on the lateral aspect of the femur that will serve as the anchoring point for a femoral jig to guide femoral component placement.

Figure 7:
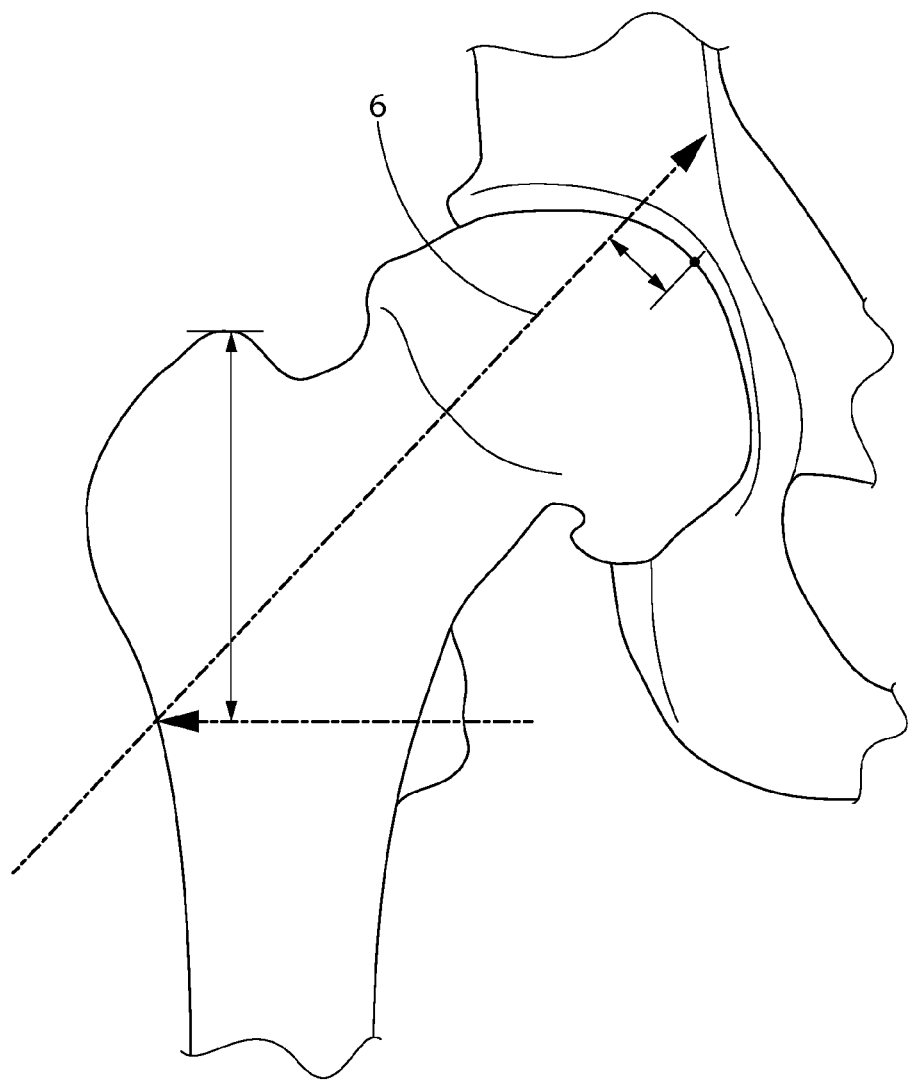
FIG. 7 is an x-ray image showing determination of an anchor point for the femoral jig, another aspect of the third step in the measurement and component placement process, in accordance with one embodiment of the present invention.

FIG. 7 also shows the third step that continues with the measurement of the exit point 7 of the lateral femur in relation to the lesser trochanter. This figure illustrates that the anchor point described above in FIG. 6 can also be characterized in relation to the lesser trochanter. This characterization provides a second visual confirmatory landmark intraoperatively for the operating surgeon to support correct placement of the lateral anchoring pin for the femoral jig.

Figure 8:
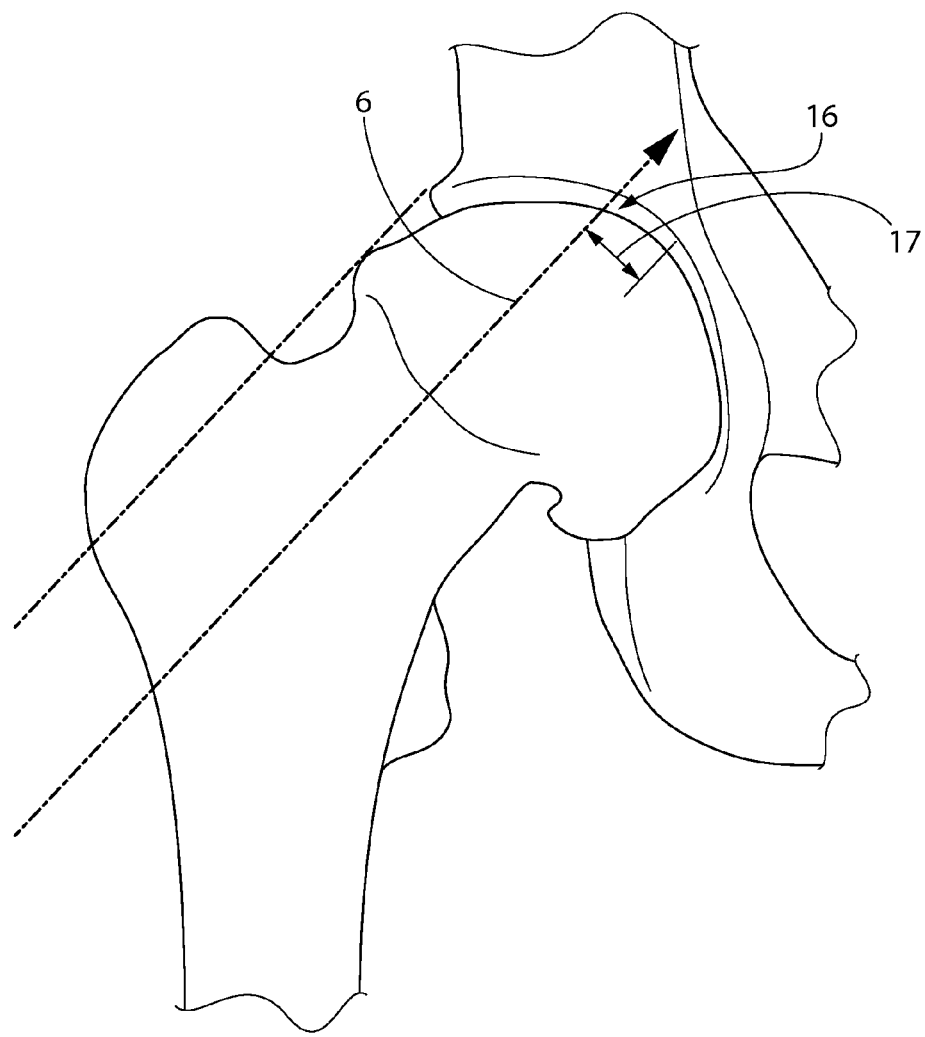
FIG. 8 is an x-ray image showing determination of the entry point for the femoral centering pin in the cranial-caudal dimension, a fourth step in the measurement and component placement process, in accordance with one embodiment of the present invention.

The next step involves the measurement of the distance from the superior aspect of the fovea to the entry point of the femoral component centering pin on the superior femoral head. This entry point is being defined here in relation to the cranial caudal dimension of the femoral head. The fourth step shown in FIG. 8 includes confirming the distance 17 of the exit point 16 on the superior femoral neck in relation to the top of the fovea on the femoral head. In the example shown in FIG. 8, this distance 17 is 16.07 mm. The initial arrow 6 drawn through the femoral neck that exits the superior femoral head will have a certain distance 13 above the patient's fovea, an ovoid depression in the head of the femur. This distance can be measured with a ruler and it can also be reproduced in the operating room. Once this is done, the surgeon has two fixed landmarks, the lateral femoral cortex as well as the superior femoral head that will determine where the exit point for the pin should be. Once these two fixed points have been reproduced, the varus/valgus position of the femoral component of the hip resurfacing construct can be very accurately positioned.

Figure 9:
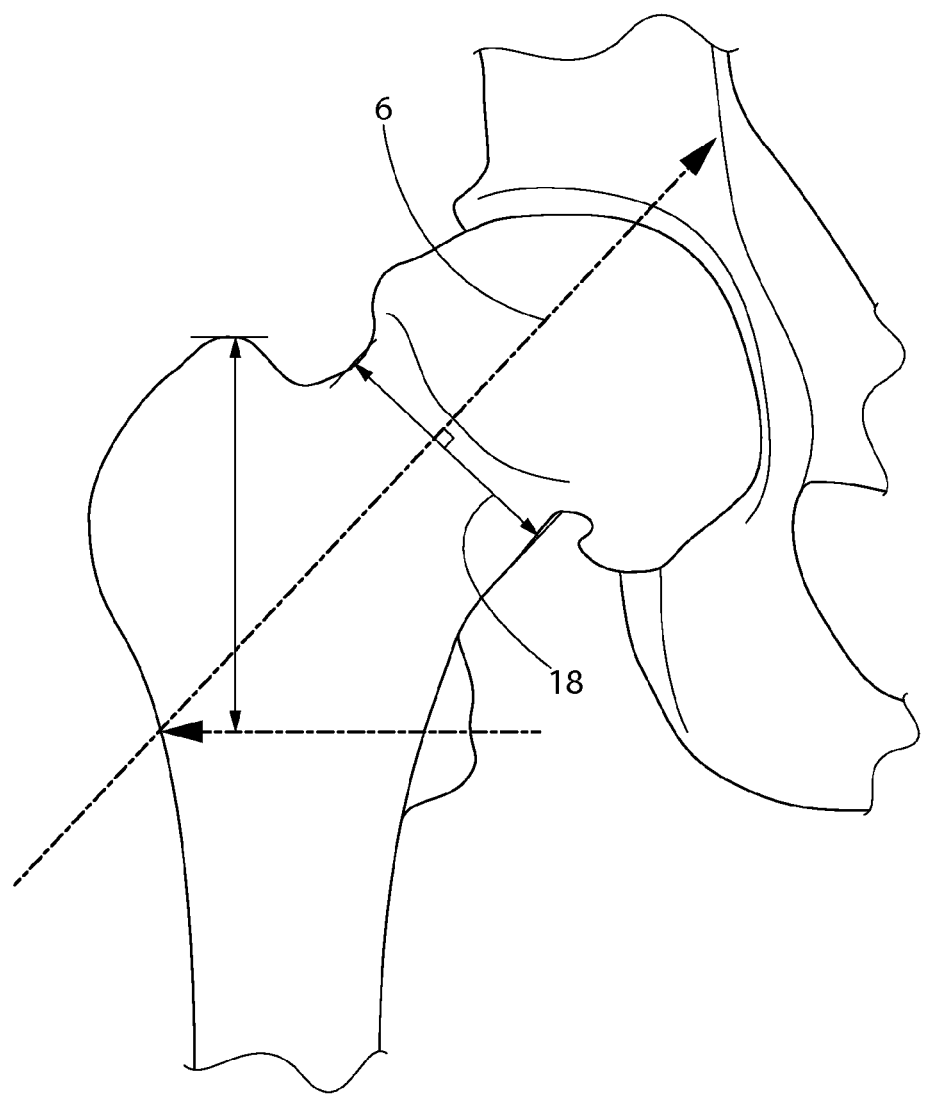
FIG. 9 is an x-ray image showing confirmation of the correct placement of the femoral centering pin, a fifth step in the measurement and component placement process, in accordance with one embodiment of the present invention.

FIG. 9 shows the fifth step that involves confirming the centered placement of the femoral component centering pin in the femoral head in the cranial-caudal dimension. In this step, the surgeon determines the setting of the femoral component jig that must fit on the patient's femoral neck intraoperatively if the superior pin entry point is correctly centered. This involves measurement of the femoral neck at its maximum diameter. This should be done at the midpoint of the femoral neck using a ruler alignment that is perpendicular to the long arrow drawn in the center of the femoral neck. By setting this perpendicular, the surgeon will have an idea what is the maximum diameter of the femoral neck around which the jig from the Birmingham hip resurfacing component should be centered. For example, if the patient has a size 56 femoral head that has a femoral neck that is 44 mm in diameter, then the surgeon will attempt to center intraoperatively the Birmingham hip measuring device on the 44 mm diameter. If he is successful in reproducing the lateral entry point site followed by the superior femoral head exit site followed by centering the Birmingham hip circular femoral neck measuring device, then he is nearly confirmed that he has centered the pin around the patient's femoral neck and that he has adequate varus/valgus positioning. In the example shown in FIG. 9, this distance 18 is about 39.78 mm.

Figure 10:
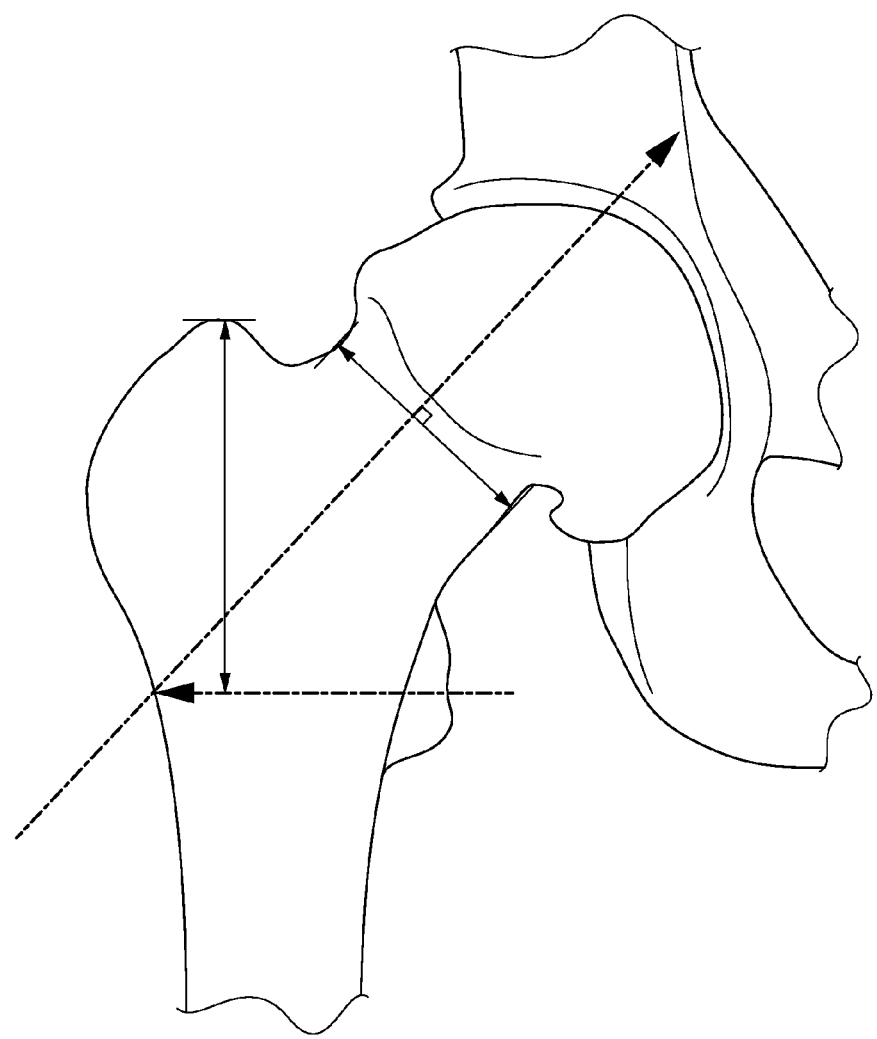
FIG. 10 is an x-ray image showing measurement of the femoral neck in the presence of ostephytes, a sixth step in the measurement and component placement process, in accordance with one embodiment of the present invention.

FIG. 10 is an x-ray image showing measurement of the femoral neck in the presence of osteophytes, a sixth step in the measurement and component placement process, in accordance with this embodiment of the present invention. This illustrates that use of this templating method allows the operating surgeon to avoid mistakes in measurement of femoral neck dimensions as a result of osteophytes that have developed on the femoral neck from the arthritic disease process. Such osteophytes are extremely difficult to differentiate intraoperatively from normal bone. By confirming this measurement, the risk of focus on the femoral neck osteophytes is obviated, and allows highly accurate centering of femoral components. One common mistake is for surgeons to center the femoral component using osteophytes. Such practice can result in poor alignment of the femoral component with subsequent femoral neck damage and component failure, and can be avoided with the current method.

Figure 11:
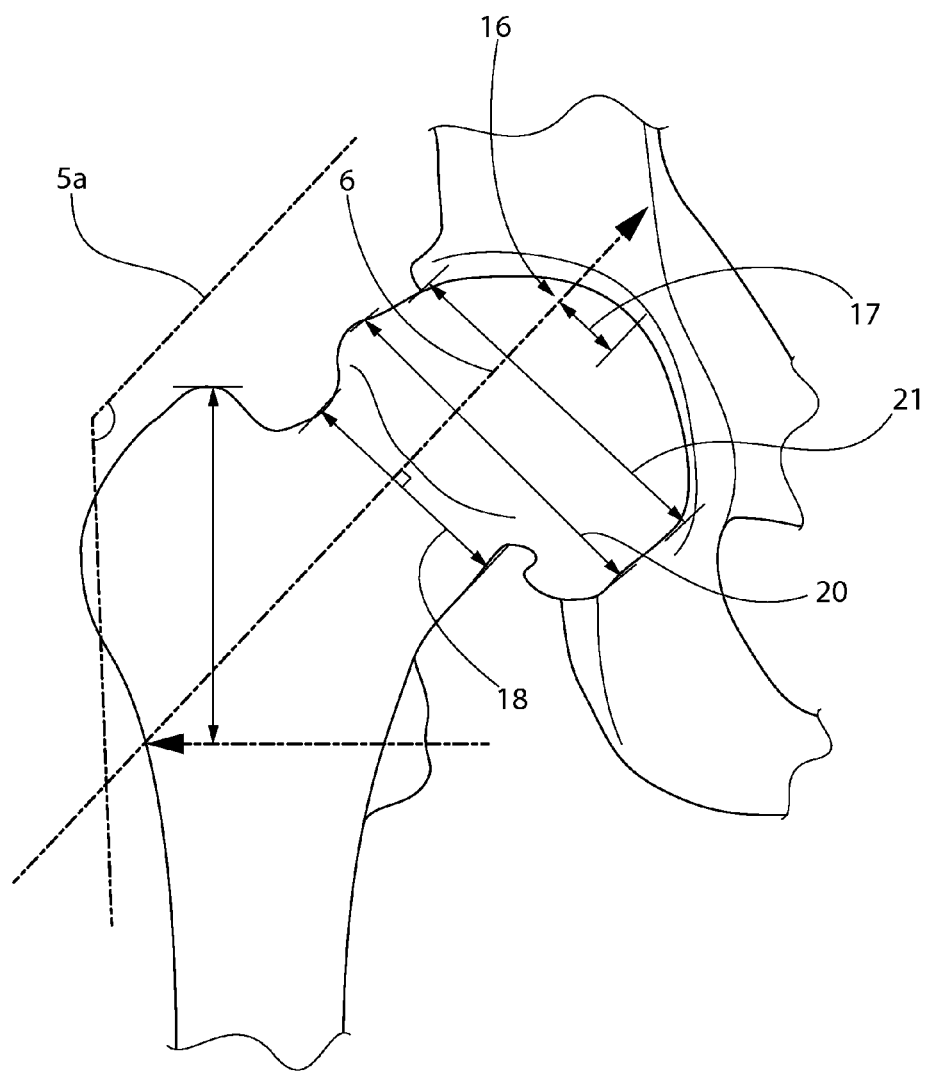
FIG. 11 is an x-ray image showing a final anterior-posterior template obtained in the measurement and component placement process, in accordance with one embodiment of the present invention.

FIG. 11 is an x-ray image showing a final anterior-posterior template obtained to this point in the measurement and component placement process, in accordance with this embodiment of the present invention. Also illustrated on this figure are lines 20 (a distance of about 49.90 mm) and 21 (a distance of about 54.77 mm). Line 20 is a measurement of the patient's actual femoral head diameter in anterior posterior x-ray projection. This measurement gives the operating surgeon a close estimate of the target resurfacing femoral component head size that should be used. Line 21 is a measurement of the patient's actual acetabular diameter in anterior posterior x-ray projection. This measurement gives the operating surgeon a close estimate of the target resurfacing acetabular component head size that should be used. From this point, the next series of steps relate to the measurement of the receptive portion of the pelvis in order to fit and position the hemispherical cup portion of the hip arthoplasty.

Figure 12:
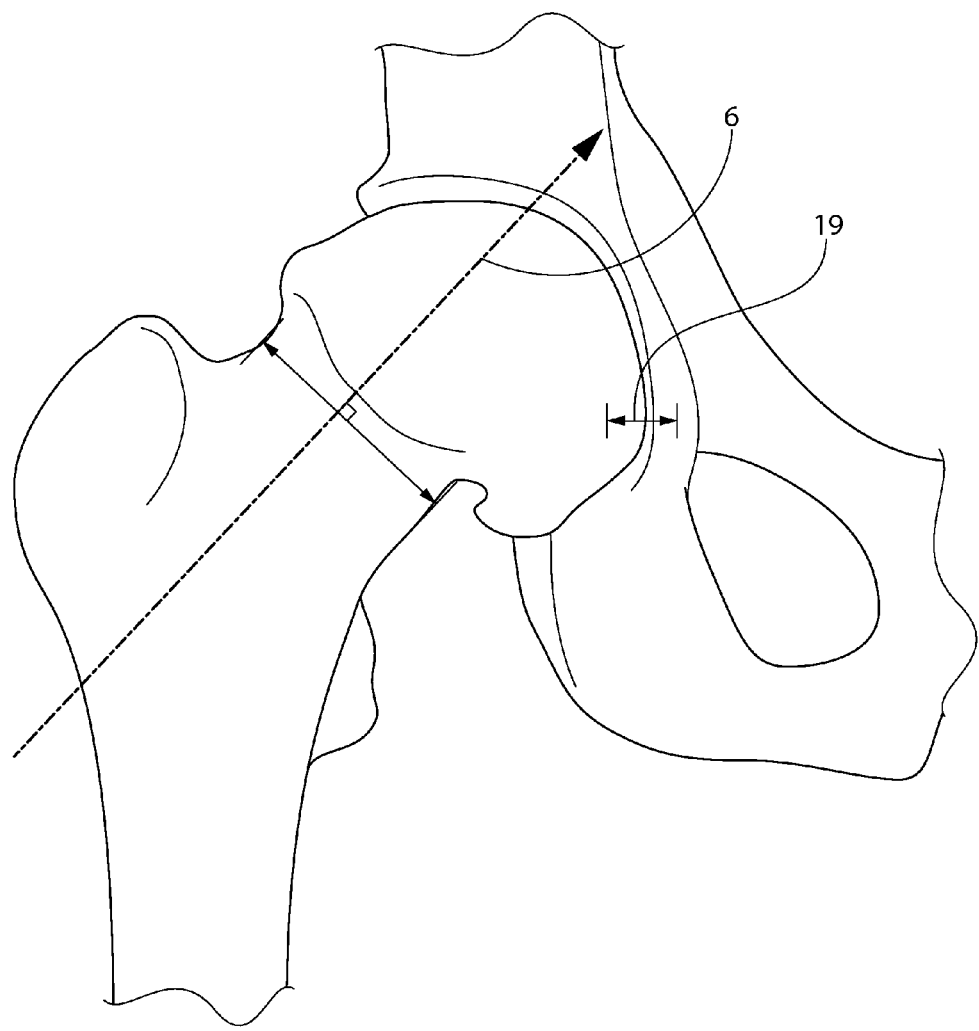
FIG. 12 is an x-ray image showing the determination of the medialization of the acetabular component, a seventh step in the measurement and component placement process in accordance with one embodiment of the present invention.

FIG. 12 shows the seventh step that involves the measurement of the distance of medialization 19 of the acetabular component for maximal bony coverage and ingrowth surface. Specifically, it illustrates accurate measurement of the amount of bone that should be reamed away from the medial wall of the acetabulum. In the example shown in FIG. 12, this distance 19 is 11.18 mm.

Figure 13:
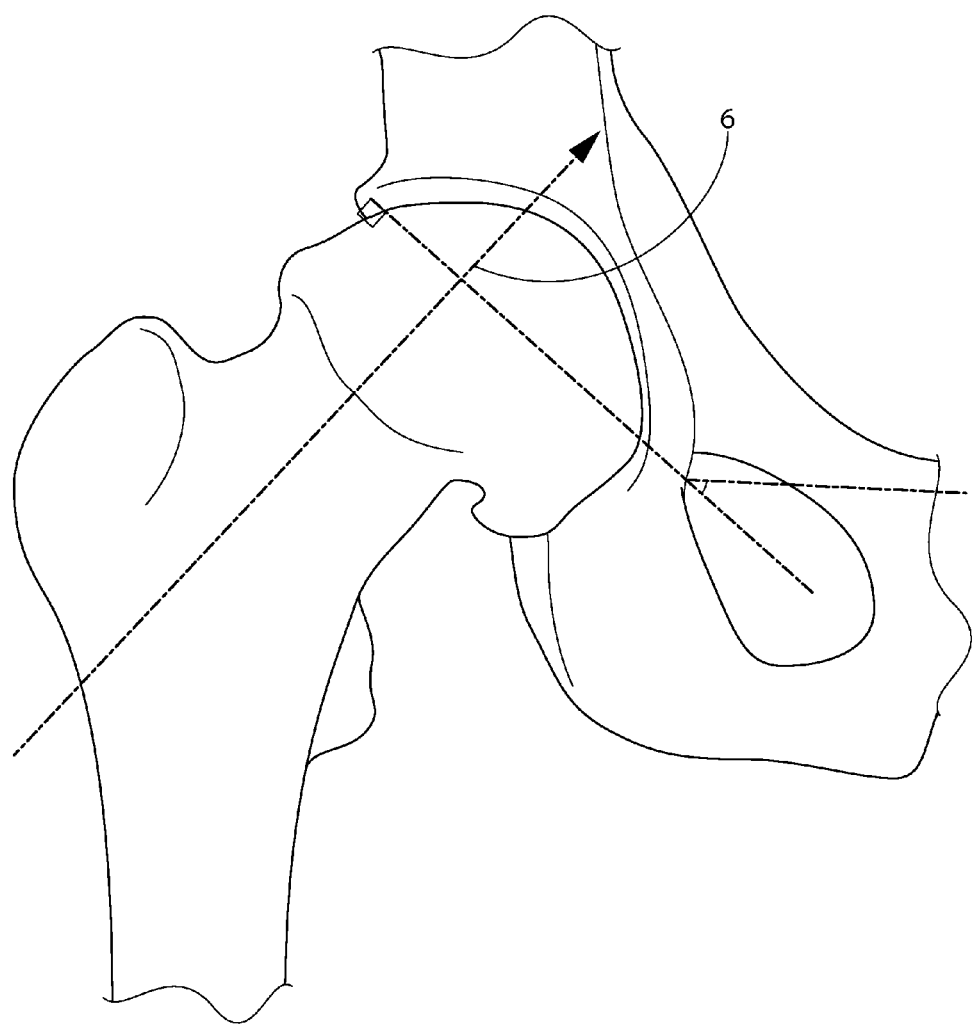
FIG. 13 is an x-ray image showing the orientation of the acetabular component of the prosthetic hip system, an eighth step in the measurement and component placement process, in accordance with one embodiment of the present invention.

FIG. 13 is an x-ray image showing a further eighth step, that being the computation of the "combined abduction" angle of the cup and stem, derived from the valgus of the stem. This will be the angle at which the acetabular component should be placed to result in orthogonal orientation of the cup and prosthetic femoral head to one another in the coronal plane. In the example shown in FIG. 13, this angle is about 39 degrees.

Figure 14:
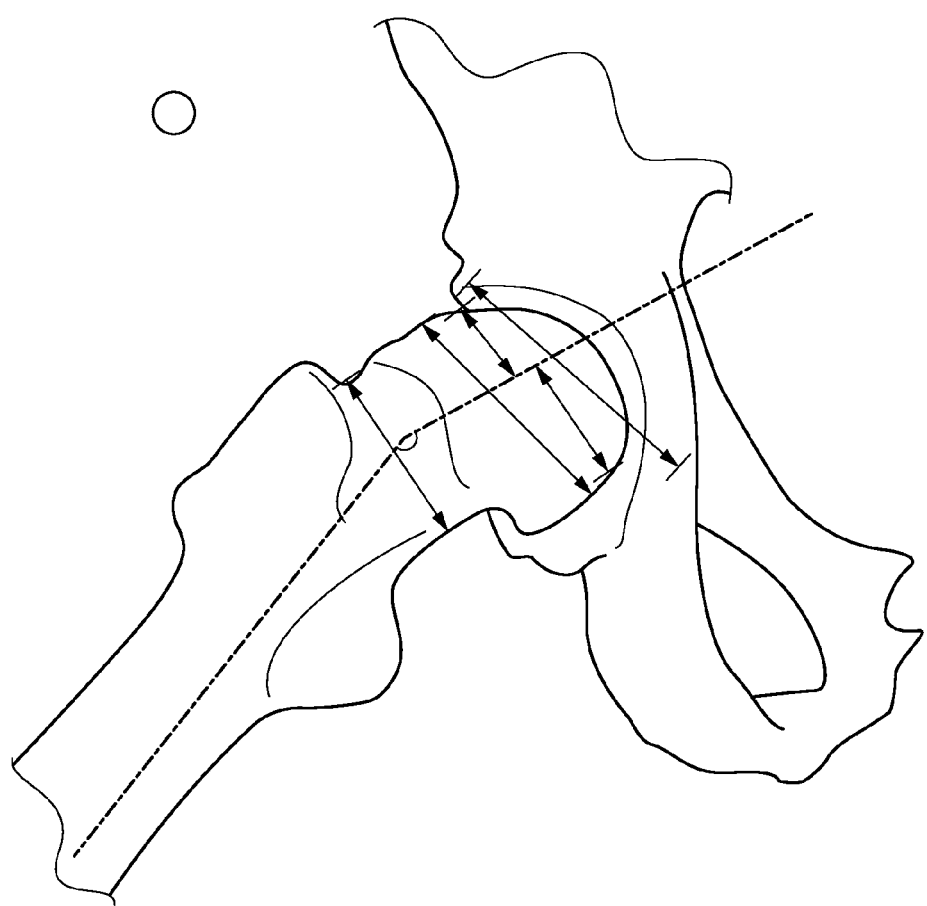
FIG. 14 is an x-ray image showing the determination of the anteversion of the acetabular and femoral components of the prosthesis, a ninth step in the measurement and component placement process, in accordance with one embodiment of the present invention.

In the ninth step shown in FIG. 14, the lateral x-ray image may be viewed to confirm the scaling marker in order to provide a secondary check of the component sizing. It is also used to determine the desired anteversion of both the femoral component and the acetabular component as described below.

Figure 15:
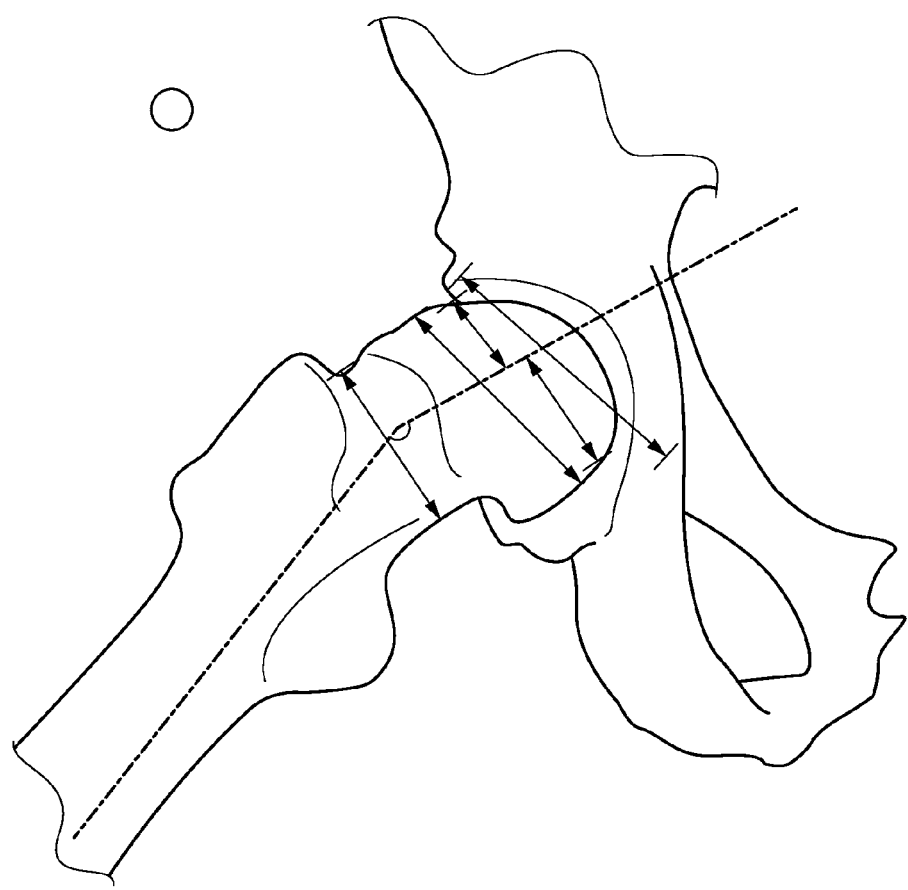
FIG. 15 is an x-ray image showing the determination of the native anteversion of the patient's femoral neck, a tenth step in the measurement and component placement process, in accordance with one embodiment of the present invention

FIG. 15 shows showing a tenth step that includes the measurement of the patient femoral neck and exit point in the lateral x-ray view, and also allows the measurement of the "combined anteversion" of the cup and stem. This figure shows that a line in the center of the femoral neck on a lateral x-ray is used to determine the native anteversion of the patient's femoral neck. The operating surgeon can use this native anteversion as a reference point intraoperatively. The method we use here suggests that the surgeon attempt to reproduce the patient's native femoral neck anteversion with placement of the prosthetic femoral component in the same orientation.

Figure 16:
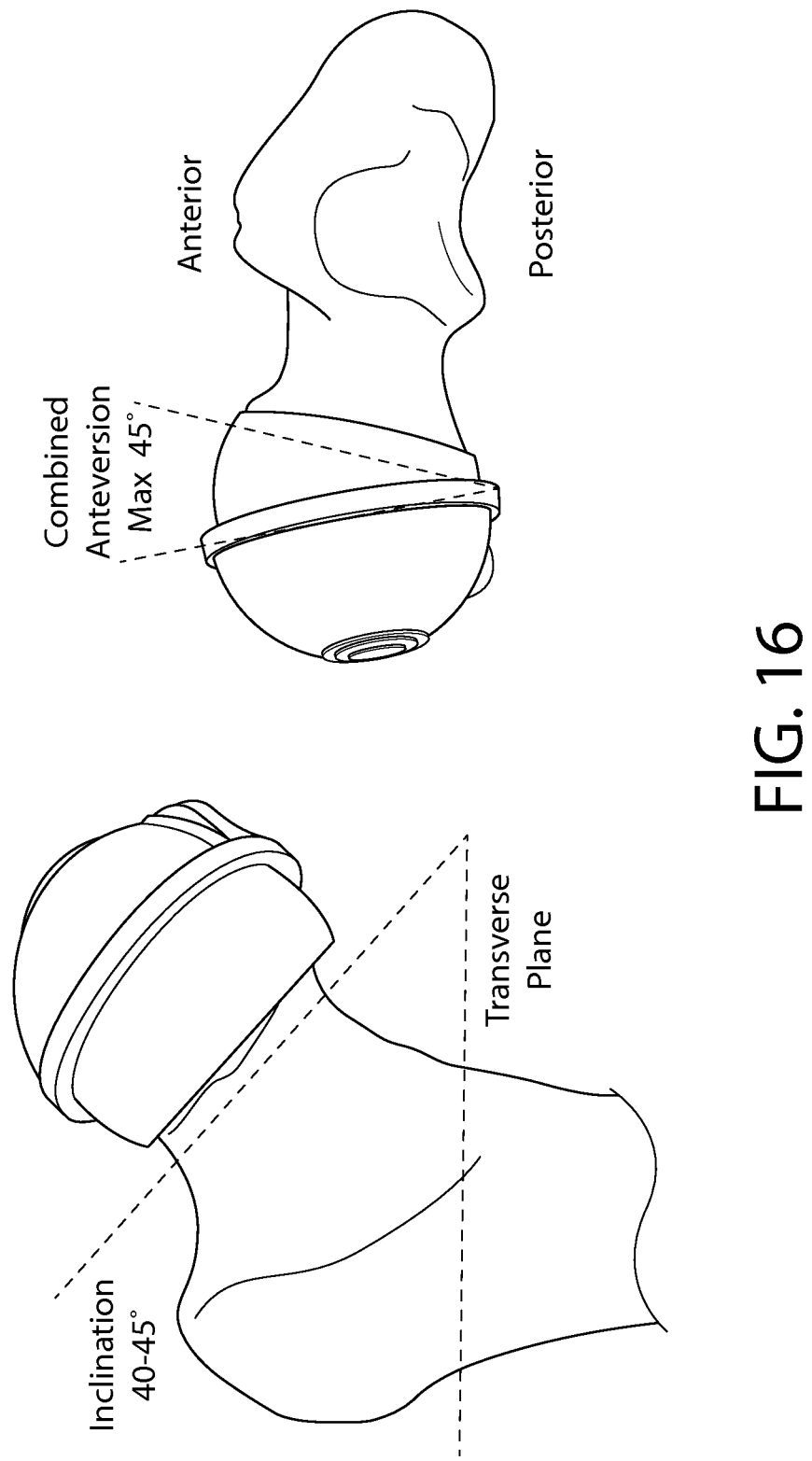
FIG. 16 is a solid model image showing the measurement and importance of combined anteversion in the placement of hip resurfacing component placement in the practice of the present invention.

Subsequent to FIG. 15, by determining the patient's native anteversion, and also placing the prosthetic femoral component in this same anteversion, the surgeon can then determine the target anteversion of the acetabular component to achieve a "combined anteversion" of between 30 and 45 degrees. FIG. 16 is a solid model image showing the measurement and importance of combined anteversion in the placement of hip resurfacing component placement in the practice of this present invention. The resurfacing literature is quite clear that a target combined anteversion of between 30 and 45 degrees will optimize function and longevity of the implant. For example, a combined anteversion greater than 45 degrees is to be avoided to reduce the risk of edge loading. Additionally, such target combined anteversion will result in the orthogonal placement of the femoral and acetabular components in the sagittal plane.

Figure 17:
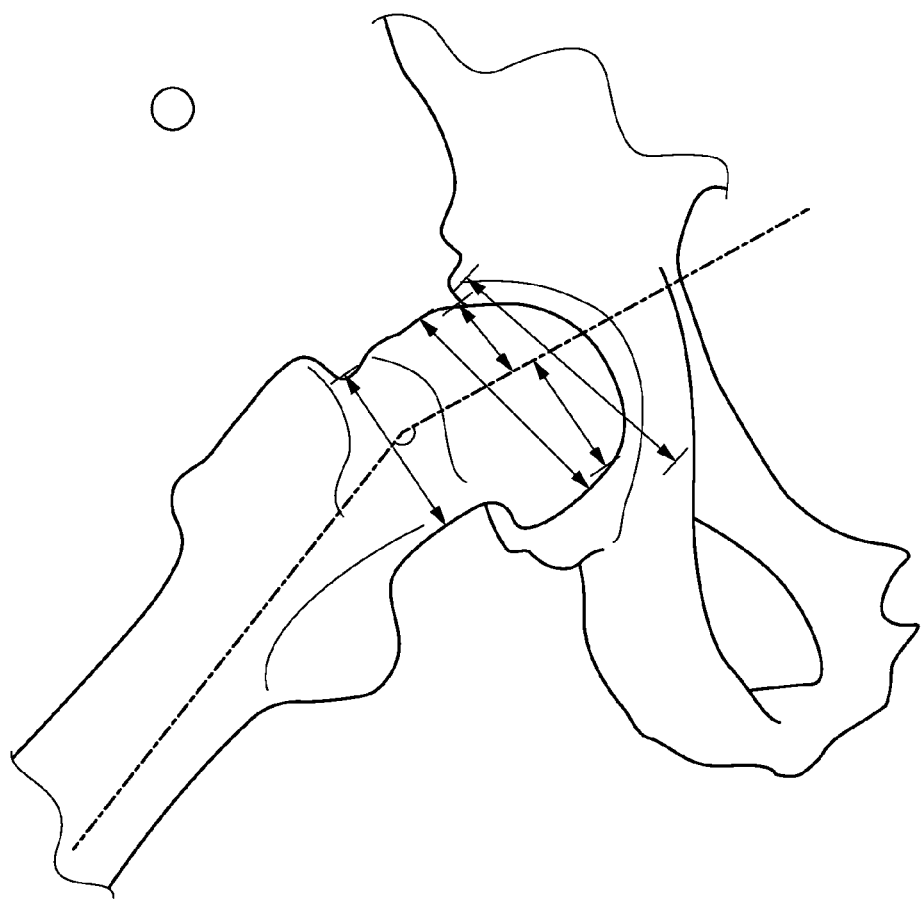
FIG. 17 is an x-ray image showing the determination of the entry point for the femoral centering pin in the anterior-posterior dimension, another aspect of the tenth step in the measurement and component placement process, in accordance with one embodiment of the present invention.

FIG. 17 is an x-ray image showing the continuation of the tenth step in the measurement and component placement process, and involves identifying the femoral guide pin exit point on the femoral head with relation to the anterior and posterior aspects of the patient's native femoral head. This figure illustrates that the surgeon can identify the appropriate femoral pin entry point that was previously described in FIG. 8 in the cranial-caudal dimension on the lateral x-ray. It illustrates the entry point in relation to the femoral head in its anterior-posterior dimension. By identifying the entry point of this pin on both the anterior-posterior and cranial-caudal dimensions, the operating surgeon can successfully reproduce this desired pin placement intraoperatively.

Figure 18:
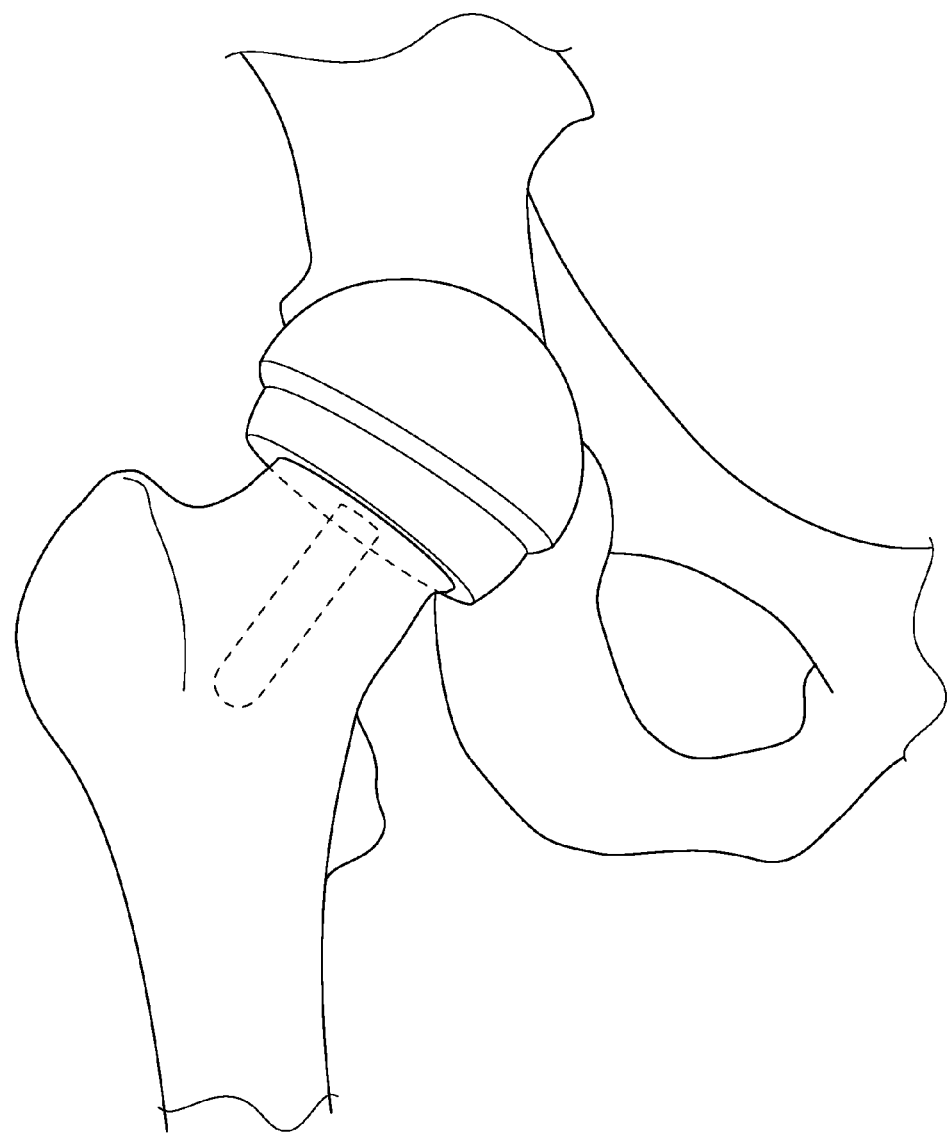
FIG. 18 is an x-ray image showing the position of the hip resurfacing components placed in accordance with one embodiment of the measurement and component placement process of the present invention.

FIG. 18 is an x-ray image showing the position of the hip resurfacing components placed in accordance with this embodiment of the measurement and component placement process of the present invention.

Figure 19:
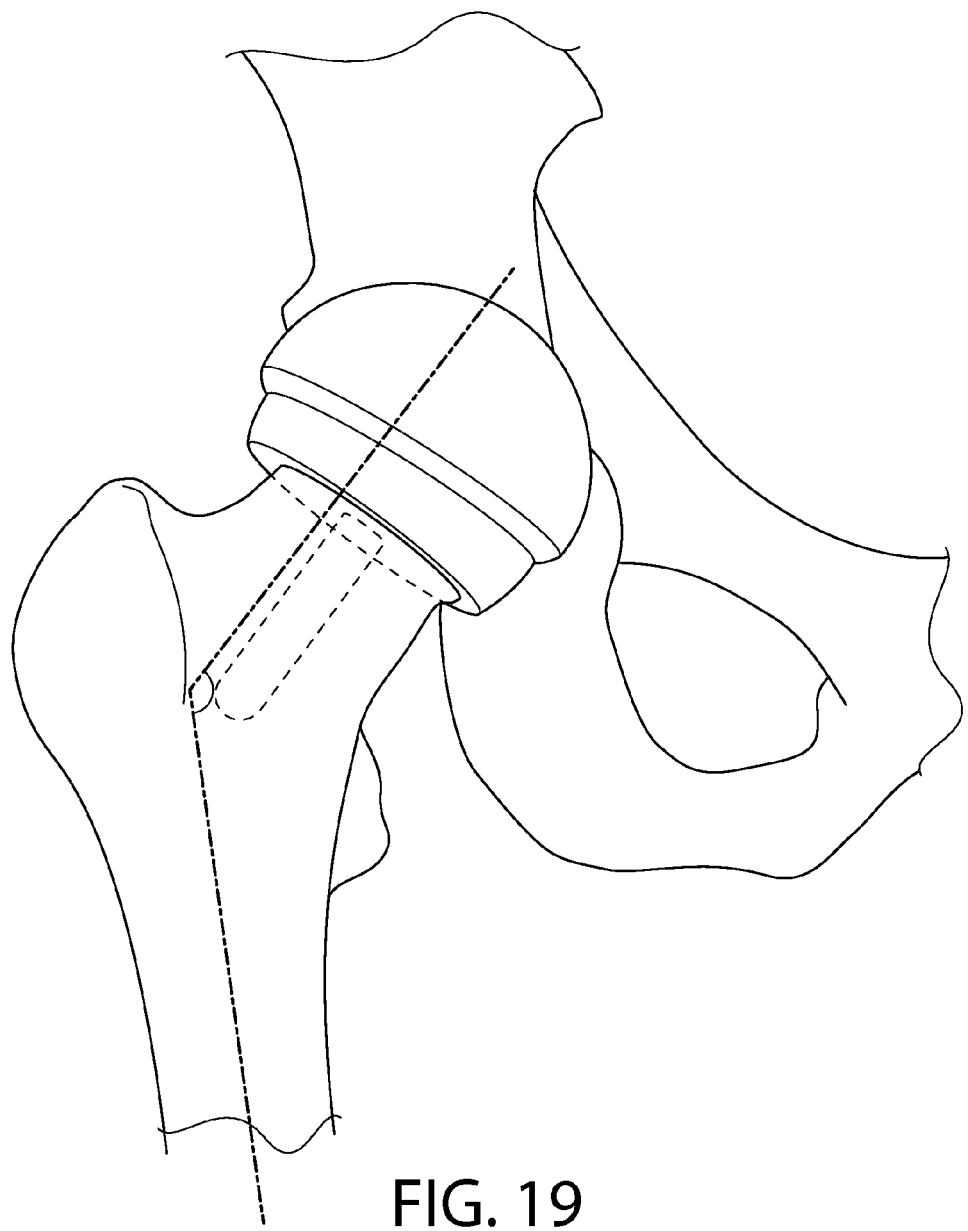
FIG. 19 is an x-ray image showing the position of the hip resurfacing components, with conformance of placement angle, placed in accordance with one embodiment of the measurement and component placement process of the present invention.

FIG. 19 is an x-ray image showing the position of the hip resurfacing components, confirming the stem placement angle as originally measured and determined (i.e., 136 degrees).

Figure 20:
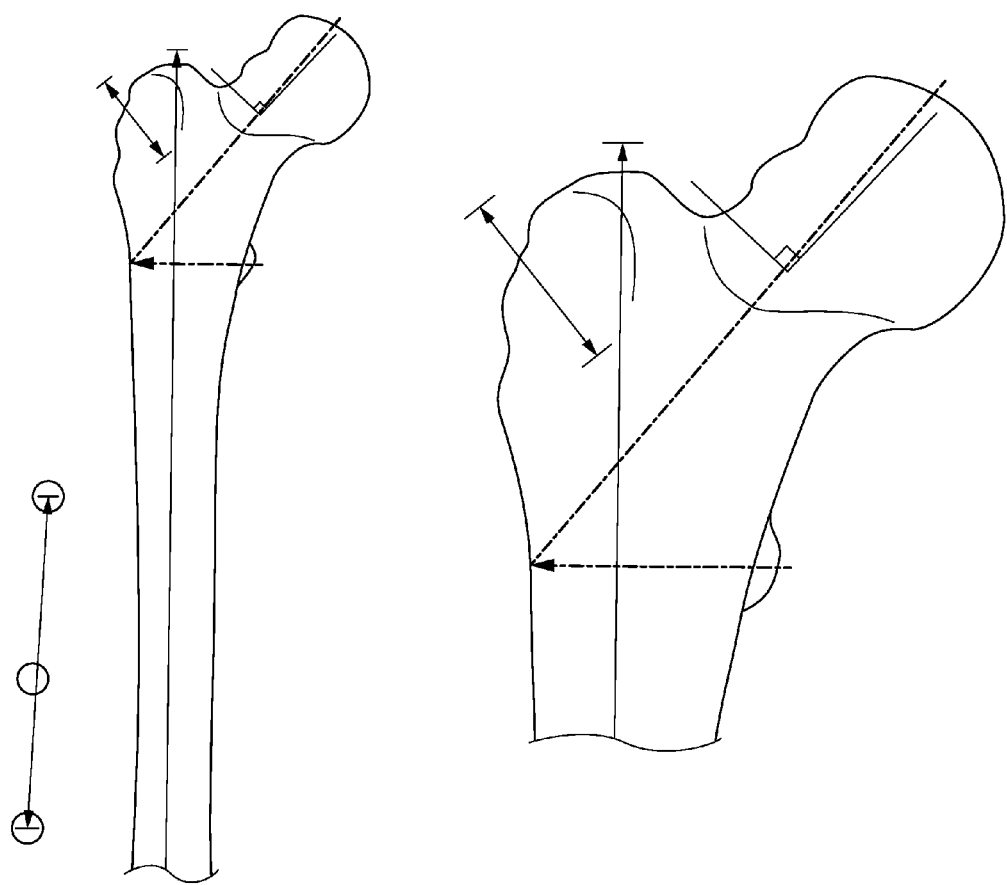
FIG. 20 is an x-ray image showing cadaveric confirmation of the results of the measurement process, in accordance with one embodiment of the present invention.

FIG. 20 is an x-ray image showing cadaveric confirmation of the results of the measurement process as carried out in accordance with this embodiment of the present invention.

Figure 21:
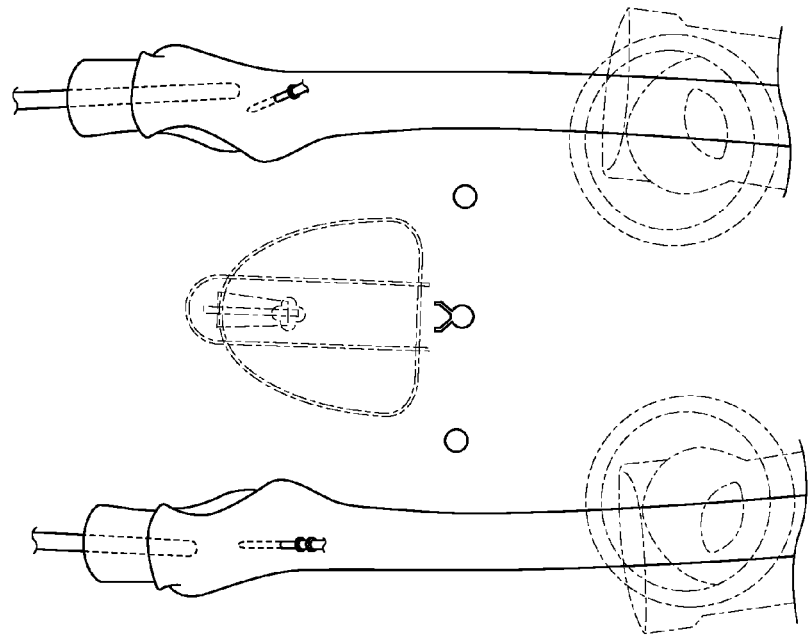
FIG. 21 is an x-ray image showing a femur view of comparative post-reaming results of the measurement and component placement process, showing placed in accordance with one embodiment of the measurement and component placement process of the present invention.
Figure 21:
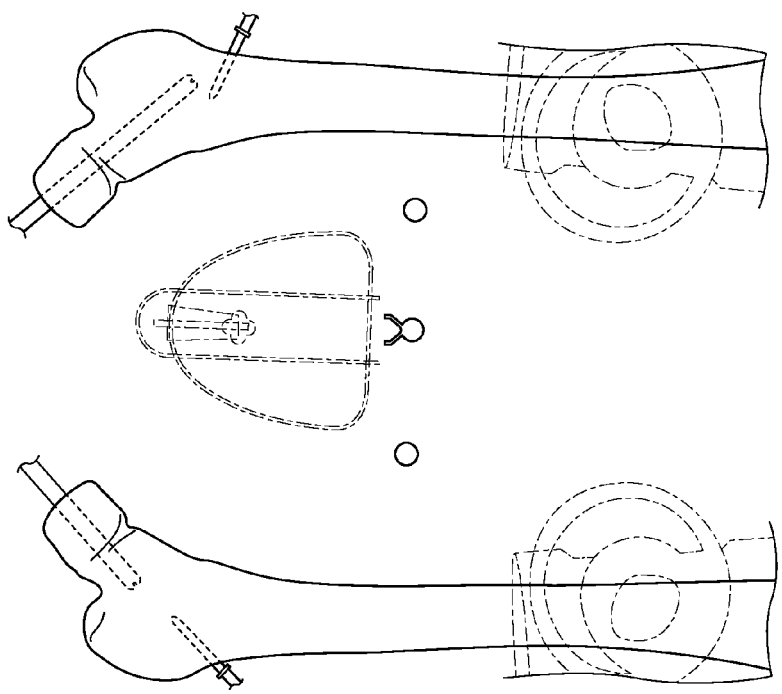

FIG. 21 is an x-ray image showing a femur view of comparative post-reaming results of the measurement and component placement process, showing placed in accordance with one embodiment of the measurement and component placement process of the present invention. This figure illustrates two matched cadaveric femora that have been reamed. The femur on the left of the figure has been prepared and reamed utilizing the method of the present invention. It is clear that the femoral neck has not been damaged at all by using this method. The femur on the right of the figure has been prepared using an alternative method that has clearly resulted in significant damage to the inferior femoral neck.

Figure 22:
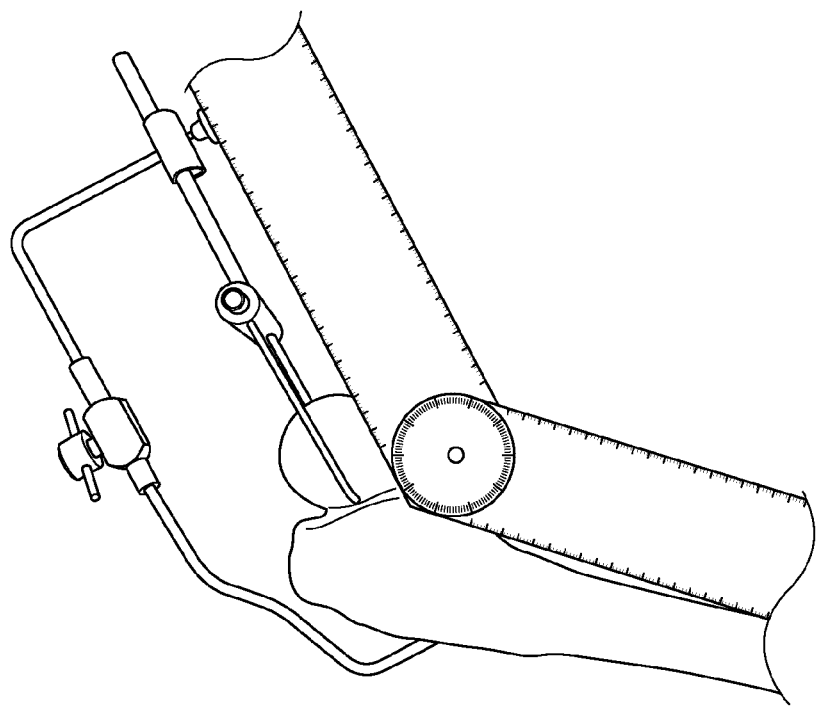
FIG. 22 show photographs showing the conformance of angular and positional measurement and component placement process using hip resurfacing component placement hardware.
Figure 22:
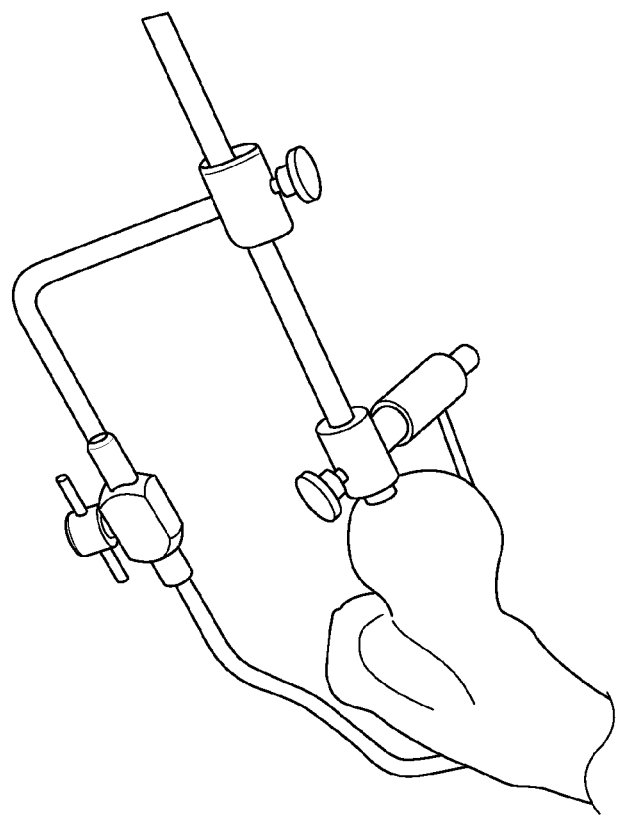

FIG. 22 show photographs showing the conformance of angular and positional measurement and component placement process using hip resurfacing component placement hardware, such as the angled ruler. This photograph also illustrates a femoral jig that could be utilized with the method of the present invention.

Once the foregoing measurement steps have been completed, these measurements may be used by the surgeon by translating these measurements to the actual constituent bones of the patient, such as through physical marking, and taking action to position and install the hip resurfacing component hardware.

This may be done using measuring and marking tools, such as rulers and known marking devices, as well as jigs and reaming tools known and used in the field.

The method of the present invention was practiced in 70 SRAs that were planned and performed in 67 patients utilizing the posterolateral surgical approach and x-ray images from PACS based plain radiographic templating technique for femoral and acetabular component positioning. The results were similar to that shown in FIGS. 19 and 20 wherein the final femoral and acetabular component positioning accurately reflected the initial angle of insertion and intended combined anteversion.

The first 70 SRAs were the first 70 performed by a surgeon from the beginning of that surgeon's SRA series. Two patients had bilateral SRAs performed. The average patient age was 53 years (range 33-71), while the average BMI was 27.8 (range 23-38). The 67 patients included 60 men and 7 women. Four patients were converted intraoperatively to total hip arthroplasty secondary to large femoral head cysts that preclude femoral component fixation, leaving 66 SRAs that were performed.

The SRAs resulted in no incidences of femoral notching and no femoral fractures. The average follow-up in the series was 6.5 months. The average acetabular abduction was 40.1 degrees (range 27-54), and the anteversion average was 31.5 (range 20-50).

There were also no instances of contact of the distal tip of the femoral stem with the cortical bone of the femoral neck. Only one acetabular component had an abduction angle higher than 45 degrees. Only one femoral component had a valgus angle that was less than or equal to the patient's native femoral neck.

No infections resulted, nor were any revisions required or indicated.

It will be appreciated that the logical order of the steps are used for purposes of illustration only, and that the measurements and determinations may be varied where not otherwise inconsistent with the purpose and result obtained in the practice of the invention.

The invention may be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description, and all changes that come within the meaning and range of equivalency of the claims are intended to be embraced therein.

The present invention may be used in accordance with other methods and devices relating to hip resurfacing operations, such as those described in the following references that are hereby incorporated herein by reference:

1. 20110190775 Device and method for achieving accurate positioning of acetabular cup during total hip replacement
2. 20110004318 Method And Apparatus For Hip Femoral Resurfacing Tooling
3. 20100274253 Device and method for achieving accurate positioning of acetabular cup during total hip replacement
4. 20100125340 Acetabular cup with supplemental screw fixation using conical interference fit between screw and cup
5. 20100121458 Femoral Head Resurfacing
6. 20090222015 Hip Resurfacing Surgical Guide Tool
7. 20090048681 Hip Resurfacing Implant
8. 20080262626 Femoral sleeve for hip resurfacing
9. 20080200991 Resurfacing femoral head component
10. 20080125785 Targeting Device
11. 20080109085 Method and apparatus for hip femoral resurfacing tooling
12. 20080033577 Hip Resurfacing Component
13. 20080009951 Femoral head resurfacing implant with internal plate fixation and instrumentation
14. 20080004710 Femoral head resurfacing
15. 20060189864 Computer-assisted hip joint resurfacing method and system
16. U.S. Pat. No. 8,078,440 Operatively tuning implants for increased performance
17. D642,263 Arthroplasty jig blank
18. U.S. Pat. No. 7,909,882 Socket and prosthesis for joint replacement
19. U.S. Pat. No. 7,887,831 Bone enhancing composite
20. U.S. Pat. No. 7,885,705 System and method for facilitating hip surgery
21. U.S. Pat. No. 7,879,106 Hip joint prosthesis
22. U.S. Pat. No. 7,867,281 Metallic bearings for joint replacement
23. U.S. Pat. No. 7,837,621 Computer-aided bone distraction
24. U.S. Pat. No. 7,819,879 Guide pin placement for hip resurfacing
25. U.S. Pat. No. 7,819,875 Surgical devices and methods of use
26. U.S. Pat. No. 7,695,476 Head centering jig for femoral resurfacing
27. U.S. Pat. No. 7,641,656 Prosthetic cup
28. U.S. Pat. No. 7,572,295 Cushion bearing implants for load bearing applications
29. U.S. Pat. No. 7,361,194 Metallic bearings for joint replacement
30. U.S. Pat. No. 7,169,185 Canine acetabular cup
31. U.S. Pat. No. 6,711,432 Computer-aided orthopedic surgery
32. U.S. Pat. No. 6,701,174 Computer-aided bone distraction
33. U.S. Pat. No. 6,626,949 Diamond coated joint implant
34. U.S. Pat. No. 6,595,999 Drilling jig for the determination of the axis of a femur head prosthesis
35. U.S. Pat. No. 6,136,034 Enarthrodial type joint socket implant
36. U.S. Pat. No. 6,096,084 Modular ball and socket joint preferably with a ceramic head ball
37. U.S. Pat. No. 4,715,860 Porous acetabular hip resurfacing

What is claimed is:

1. A method of positioning components during the course of a hip resurfacing operation for a patient, involving affixation of a femoral cap to the patient's femoral head and the affixation of an acetabular component implant in a corresponding reamed and prepared acetabulum of the patient's pelvis, the method comprising:

a. in a scaled anterior-posterior x-ray image of the patient's femur and pelvic region:

i. providing a center line along a center axis of the patient's femoral neck so as to indicate a position of a femoral lateral pin entry point and a location of a point of intersection of said center line with the patient's superior femoral head surface;

ii. measuring a varus/valgus angle of the femoral neck with respect to the femur so as to determine a desired varus/valgus angle of insertion of the femoral cap with respect to the femoral neck;

iii. providing additional lines parallel to said center line so as to determine a desired size of the femoral cap to be affixed and thereby to permit a determination of a size of a femoral reamer to be used in the hip resurfacing operation;

iv. measuring a maximum diameter of the femoral neck that is determined by the providing of the parallel lines described in step (iii.);

v. determining a notching distance corresponding to superior femoral head and superior femoral neck positions; such distance being an exact distance from an exit point of the femoral reamer used to prepare the femoral head for receipt of the femoral cap to a piriformis fossa portion of cortical bone of the femoral neck;

vi. determining a vertical distance from a tip of the patient's greater trochanter to the femoral lateral pin entry point;

vii. determining an exact location of the entry point of the femoral lateral pin in relation to a cranial-caudal dimension of the patient's lesser trochanter;

viii. determining a distance from said point of intersection in step (i.) to a superior point of fovea on the femoral head; and ix. measuring a cup closure angle so as to match the varus/valgus angle of the femoral neck so as to facilitate combined abduction; the combined abduction being such that a face of the acetabular component implant is perfectly perpendicular to the center axis of the femoral neck; and b. in a scaled lateral x-ray image of the femur and pelvic region:

i. drawing a centering line along the center axis of the femoral neck so as to select an anteversion/retroversion angle of the femoral head;

ii. measuring both an anteversion angle of the centering line as well as a distance and a position of an exit point of the centering line from anterior and posterior margins of the femoral head; and iii. calculating an anteversion of said centering line with respect to a shaft of the femur; said anteversion then being used to calculate a target combined anteversion of between about 35 and about 45 degrees for the acetabular and femoral components; whereby positioning parameters attendant to the hip resurfacing operation are determined; and c. completing said hip resurfacing operation in accordance with said hip resurfacing operation positioning parameters.

2. The method according to claim 1 additionally comprising marking the femur of said patient in accordance with the positioning parameters determined in steps (a.) and (b.), and inserting the femoral cap in said patient using the positioning parameters determined in steps (a.) and (b.).

3. The method according to claim 1 additionally comprising marking the femur in accordance with the positioning parameters determined in steps (a.) and (b).

4. The method according to claim 1 additionally comprising reaming the femoral head with the femoral reamer, the size of which is determined by reference to said parallel lines.

5. A method of positioning components during the course of a hip resurfacing operation for a patient, involving affixation of a femoral cap to the patient's femoral head and affixation of an acetabular component implant in a corresponding reamed and prepared acetabulum of the patient's pelvis, the method comprising:

a. in a scaled anterior-posterior x-ray image of the patient's femur and pelvic region:

i. providing a center line along a center axis of the patient's femoral neck so as to indicate a position of a femoral lateral pin entry point and a location of a point of intersection of said center line with the patient's superior femoral head surface;

ii. measuring a varus/valgus angle of the femoral neck with respect to the femur so as to determine a desired varus/valgus angle of insertion of the femoral cap with respect to the femoral neck;

iii. providing additional lines parallel to said center line so as to determine a desired size of the femoral cap to be affixed and thereby to permit a determination of a size of a femoral reamer to be used in the hip resurfacing operation;

iv. measuring a maximum diameter of the femoral neck that is determined by the providing of the parallel lines described in step (iii.);

v. determining a notching distance corresponding to superior femoral head and superior femoral neck positions; such distance being an exact distance from an exit point of the femoral reamer used to prepare the femoral head for receipt of the femoral cap to a piriformis fossa portion of cortical bone of the femoral neck;

vi. determining a vertical distance from a tip of the patient's greater trochanter to the femoral lateral pin entry point;

vii. determining an exact location of the entry point of the femoral lateral pin in relation to a cranial-caudal dimension of the patient's lesser trochanter;

viii. determining a distance from said point of intersection in step (i.) to a superior point of fovea on the femoral head; and ix. measuring a cup closure angle so as to match the varus/valgus angle of the femoral neck so as to facilitate combined abduction; the combined abduction being such that a face of the acetabular component implant is perfectly perpendicular to the center axis of the femoral neck; and b. in a scaled lateral x-ray image of the femur and pelvic region:

i. drawing a centering line along the center axis of the femoral neck so as to select an anteversion/retroversion angle of the femoral head;

ii. measuring both an anteversion angle of the centering line as well as a distance and a position of an exit point of the centering line from anterior and posterior margins of the femoral head; and iii. calculating an anteversion of said centering line with respect to a shaft of the femur; said anteversion then being used to calculate a target combined anteversion of between about 35 and about 45 degrees for the acetabular and femoral components; whereby positioning parameters attendant to the hip resurfacing operation are determined; and c. marking the femur of said patient in accordance with the positioning parameters determined in steps (a.) and (b.), and inserting the femoral cap in said patient using the positioning parameters determined in steps (a.) and (b.).

6. A method of positioning components during the course of a hip resurfacing operation for a patient, involving affixation of a femoral cap to the patient's femoral head and affixation of an acetabular component implant in a corresponding reamed and prepared acetabulum of the patient's pelvis, the method comprising:

a. in a scaled anterior-posterior x-ray image of the patient's femur and pelvic region:

i. providing a center line along a center axis of the patient's femoral neck so as to indicate a position of a femoral lateral pin entry point and a location of a point of intersection of said center line with the patient's superior femoral head surface;

ii. measuring a varus/valgus angle of the femoral neck with respect to the femur so as to determine a desired varus/valgus angle of insertion of the femoral cap with respect to the femoral neck;

iii. providing additional lines parallel to said center line so as to determine a desired size of the femoral cap to be affixed and thereby to permit a determination of a size of a femoral reamer to be used in the hip resurfacing operation;

iv. measuring a maximum diameter of the femoral neck that is determined by the providing of the parallel lines described in step (iii.);

v. determining a notching distance corresponding to superior femoral head and superior femoral neck positions; such distance being an exact distance from an exit point of the femoral reamer used to prepare the femoral head for receipt of the femoral cap to a piriformis fossa portion of cortical bone of the femoral neck;

vi. determining a vertical distance from a tip of the patient's greater trochanter to the femoral lateral pin entry point;

vii. determining an exact location of the entry point of the femoral lateral pin in relation to a cranial-caudal dimension of the patient's lesser trochanter;

viii. determining a distance from said point of intersection in step (i.) to a superior point of fovea on the femoral head; and ix. measuring a cup closure angle so as to match the varus/valgus angle of the femoral neck so as to facilitate combined abduction; the combined abduction being such that a face of the acetabular component implant is perfectly perpendicular to the center axis of the femoral neck; and b. in a scaled lateral x-ray image of the femur and pelvic region:

i. drawing a centering line along the center axis of the femoral neck so as to select an anteversion/retroversion angle of the femoral head;

ii. measuring both an anteversion angle of the centering line as well as a distance and a position of an exit point of the centering line from anterior and posterior margins of the femoral head; and iii. calculating an anteversion of said centering line with respect to a shaft of the femur; said anteversion then being used to calculate a target combined anteversion of between about 35 and about 45 degrees for the acetabular and femoral components; whereby positioning parameters attendant to the hip resurfacing operation are determined; and c. marking the femur in accordance with the positioning parameters determined in steps (a.) and (b.).

7. A method of positioning components during the course of a hip resurfacing operation for a patient, involving affixation of a femoral cap to the patient's femoral head and affixation of an acetabular component implant in a corresponding reamed and prepared acetabulum of the patient's pelvis, the method comprising:

a. in a scaled anterior-posterior x-ray image of the patient's femur and pelvic region:

i. providing a center line along a center axis of the patient's femoral neck so as to indicate a position of a femoral lateral pin entry point and a location of a point of intersection of said center line with the patient's superior femoral head surface;

ii. measuring a varus/valgus angle of the femoral neck with respect to the femur so as to determine a desired varus/valgus angle of insertion of the femoral cap with respect to the femoral neck;

iii. providing additional lines parallel to said center line so as to determine a desired size of the femoral cap to be affixed and thereby to permit a determination of a size of a femoral reamer to be used in the hip resurfacing operation;

iv. measuring a maximum diameter of the femoral neck that is determined by the providing of the parallel lines described in step (iii.);

v. determining a notching distance corresponding to superior femoral head and superior femoral neck positions; such distance being an exact distance from an exit point of the femoral reamer used to prepare the femoral head for receipt of the femoral cap to a piriformis fossa portion of cortical bone of the femoral neck;

vi. determining a vertical distance from a tip of the patient's greater trochanter to the femoral lateral pin entry point;

vii. determining an exact location of the entry point of the femoral lateral pin in relation to a cranial-caudal dimension of the patient's lesser trochanter;

viii. determining a distance from said point of intersection in step (i.) to a superior point of fovea on the femoral head; and ix. measuring a cup closure angle so as to match the varus/valgus angle of the femoral neck so as to facilitate combined abduction; the combined abduction being such that a face of the acetabular component implant is perfectly perpendicular to the center axis of the femoral neck; and b. in a scaled lateral x-ray image of the femur and pelvic region:

i. drawing a centering line along the center axis of the femoral neck so as to select an anteversion/retroversion angle of the femoral head;

ii. measuring both an anteversion angle of the centering line as well as a distance and a position of an exit point of the centering line from anterior and posterior margins of the femoral head; and iii. calculating an anteversion of said centering line with respect to a shaft of the femur; said anteversion then being used to calculate a target combined anteversion of between about 35 and about 45 degrees for the acetabular and femoral components; whereby positioning parameters attendant to the hip resurfacing operation are determined; and c. reaming the femoral head with the femoral reamer, the size of which is determined by reference to said parallel lines.

8. A method of positioning components during the course of a hip resurfacing operation for a patient, involving affixation of a femoral cap to the patient's femoral head and affixation of an acetabular cup in a corresponding reamed and prepared acetabulum of the patient's pelvis, the method comprising:

a. in a scaled anterior-posterior x-ray image of the patient's femur and pelvic region:

i. providing a center line along a center axis of the patient's femoral neck so as to indicate a position of a femoral lateral pin entry point and a location of a point of intersection of said center line with the patient's superior femoral head surface;

ii. measuring a varus/valgus angle of the femoral neck with respect to the femur so as to determine a desired varus/valgus angle of insertion of the femoral cap with respect to the femoral neck;

iii. providing additional lines parallel to said center line so as to determine a desired size of the femoral cap to be affixed and thereby to permit a determination of a size of a femoral reamer to be used in the hip resurfacing operation;

iv. measuring a maximum diameter of the femoral neck that is determined by the providing of the parallel lines described in step (iii.);

v. determining a notching distance corresponding to superior femoral head and superior femoral neck positions; such distance being an exact distance from an exit point of the femoral reamer used to prepare the femoral head for receipt of the femoral cap to a piriformis fossa portion of cortical bone of the femoral neck;

vi. determining a vertical distance from a tip of the patient's greater trochanter to the femoral lateral pin entry point;

vii. determining an exact location of the entry point of the femoral lateral pin in relation to a cranial-caudal dimension of the patient's lesser trochanter;

viii. determining a distance from said point of intersection in step (i.) to a superior point of fovea on the femoral head; and ix. measuring a cup closure angle so as to match the varus/valgus angle of the femoral neck so as to facilitate combined abduction; the combined abduction being such that a face of the acetabular component implant is perfectly perpendicular to the center axis of the femoral neck; and b. in a scaled lateral x-ray image of the femur and pelvic region:
  i. drawing a centering line along the center axis of the femoral neck so as to select an anteversion/retroversion angle of the femoral head;
  ii. measuring both an anteversion angle of the centering line as well as a distance and a position of an exit point of the centering line from anterior and posterior margins of the femoral head; and
  iii. calculating an anteversion of said centering line with respect to a shaft of the femur; said anteversion then being used to calculate a target combined anteversion of between about 35 and about 45 degrees for the acetabular and femoral components; whereby positioning parameters attendant to the hip resurfacing operation are determined; and c. positioning the femoral cap and the acetabular cup in the patient in accordance with the positioning parameters determined in steps (a.) and (b.).

* * * * *